(12) United States Patent
Okada et al.

(10) Patent No.: US 6,458,868 B1
(45) Date of Patent: Oct. 1, 2002

(54) ORGANOPHOSPHORUS COMPOUNDS FOR DENTAL POLYMERIZABLE COMPOSITIONS

(75) Inventors: Koichi Okada; Junichi Ohtsuki; Koji Takahashi; Yasuji Minami; Eiichi Terakawa, all of Kurashiki; Miho Harada, Takatsuki, all of (JP)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/701,374

(22) PCT Filed: Mar. 30, 2000

(86) PCT No.: PCT/JP00/02002
§ 371 (c)(1),
(2), (4) Date: Nov. 30, 2000

(87) PCT Pub. No.: WO00/58316
PCT Pub. Date: Oct. 5, 2000

(30) Foreign Application Priority Data

| Mar. 31, 1999 | (JP) | 11-090662 |
| Mar. 31, 1999 | (JP) | 11-091653 |
| Apr. 1, 1999 | (JP) | 11-095145 |
| Apr. 28, 1999 | (JP) | 11-121319 |
| May 21, 1999 | (JP) | 11-141004 |

(51) Int. Cl.$^7$ .............. C08K 5/49; C07F 9/02; A61K 6/02
(52) U.S. Cl. .......... 523/116; 558/198; 526/376
(58) Field of Search .......... 523/116; 558/198; 526/376

(56) References Cited

U.S. PATENT DOCUMENTS

| 3,855,364 A | 12/1974 | Steckler |
| 5,055,497 A | * 10/1991 | Okada et al. ........ 523/116 |
| 6,300,389 B1 | * 10/2001 | Sato et al. ........ 523/116 |
| 6,315,566 B1 | * 11/2001 | Shen et al. ........ 433/226 |
| 6,350,839 B2 | * 2/2002 | Moszner et al. ....... 526/278 |

FOREIGN PATENT DOCUMENTS

| EP | 0 074 708 | 3/1983 |
| EP | 0 333 503 | 9/1989 |
| FR | 2 344 281 | 10/1977 |
| WO | 00/10478 | 3/2000 |

OTHER PUBLICATIONS

Chemical Abstracts, XP–002138412, vol. 117, No. 9, AN 090506f, Aug. 31, 1992, JP 03 294286, Dec. 25, 1991.
Chemical Abstracts, XP–002138413, vol. 098, No. 23, AN 198445p, Jun. 6, 1983, JP 58 021687, Feb. 8, 1983.
Chemical Abstracts, XP–002138414, vol. 102, No. 4, AN 032320v, Jan. 28, 1985, JP 59 129278, Jul. 25, 1984.
Research Disclosure, XP–002138411, vol. 252, No. 25215, p. 177, "Verbesserung Der Harftung Von Kunstoff An Metall(Improvement of the Adhesion of Plastics to Metals)," Apr. 1985 (with English Translation).

* cited by examiner

*Primary Examiner*—Deborah C. Lambkin
(74) *Attorney, Agent, or Firm*—Oblon, Spivak, McClelland, Maier & Neustadt, P.C.

(57) ABSTRACT

An organic phosphate compound having at least one radically polymerizable double bond, at least one phosphate residue having one or two hydroxyl groups, and at least one hydrocarbon group having 4 or more carbon atoms in a molecule, wherein a 10% by weight methanol solution of the organic phosphate compound has an electric conductivity at 25° C. of 0.5 mS/cm or less, and/or the organic phosphate compound has a light transmittance at 455 nm of 90% or more; a process for preparing the organic phosphate compound; a dental polymerizable composition comprising (a) the organic phosphate compound and (b) a polymerizable monomer capable of copolymerizing with the organic phosphate compound.

22 Claims, No Drawings

ORGANOPHOSPHORUS COMPOUNDS FOR DENTAL POLYMERIZABLE COMPOSITIONS

This application is a 371 of PCT/JP00/02002 Mar. 30, 2000

TECHNICAL FIELD

The present invention relates to an organophosphate compound (hereinafter may also be referred to as "phosphate monomer") having a polymerizable group, and a process for preparing the same, and a dental polymerizable composition comprising the organophosphate compound, the dental polymerizable composition exhibiting excellent adhesive strength.

BACKGROUND ART

A dental adhesive has been used to adhere a restorative material to a defective site of teeth or coat the site with the material, and to maintain a restorative material for a long period of time, and thus imparting great merits to present dental care services. As above, the largest reason why clinical techniques using a dental adhesive are widely spread is owing to the development of a technique for adhering to teeth, particularly to dentine tissues.

An active engagement in the studies for adhering to teeth has been made particularly since the 1970's, and particularly there have been tried applications of a polymerizable monomer having an acid group such as phosphate group or carboxylic acid group among compounds having a reactivity to hydroxyapatite, a main component of teeth. However, a phosphate monomer, which had been known at the time, for instance, 2-methacryloyloxyethyl dihydrogenphosphate, has no water resistance at all even though it was used as a dental adhesive, showing no adhesion at all to teeth, particularly to dentine tissues.

However, in the studies made by the present applicant, there have been elucidated that among monomers having a phosphate group, a phosphate monomer having a hydrocarbon group with strong hydrophobicity in the molecular structure exhibits extremely high adhesion to teeth, and high level of adhesion durability even under wet conditions such as oral cavity.

A feature of the phosphate monomers proposed by the present applicant resides in that —P(O)(OH)$_2$ group or >P(O)(OH) group is bound with a polymerizable group such as a (meth)acrylic group via a hydrocarbon group with strong hydrophobicity which has a large number of carbon atoms. The details of these technique are disclosed in the patent applications filed by the present applicant, such as Japanese Patent Laid-Open Nos. Sho 58-21607 and Sho 58-21687 (corresponding to U.S. Pat. No. 4,539,382).

It is no exaggeration to say that the technique for adhering to teeth has been established for the first time by using these phosphate monomers as a dental adhesive, which were disclosed in the above publications and the like. Since then, various forms of dental adhesives have been proposed by using a group of these phosphate monomers. The above phosphate monomers proposed by the present applicant serve a great role for imparting high adhesion achieved in these techniques.

In the preparation of the above phosphate monomers, for instance, a (meth)acrylic acid monoester monophosphate ester (hereinafter also referred to as "phosphate monoester"), there is mainly employed a preparation process comprising reacting a (meth)acrylic acid monoester, which is a reaction product of a diol and a (meth)acrylic acid, with phosphorus oxychloride, and hydrolyzing the resulting compound having —P(O)Cl$_2$ group. Such a process has been made known by the present applicant in Japanese Patent Laid-Open No. Sho 59-139392, wherein the process comprises a four-step process, steps (I) to (IV), detailed below.

(I) Preparation of (Meth)acrylic Acid Monoester

A (meth)acrylic acid monoester is prepared by esterification reaction of a diol and a (meth)acrylic acid. In this reaction, a (meth)acrylic acid diester is obtained as a by-product, and an unreacted diol is also contained in the product.

(II) Removal of Unreacted Diol in Reaction Mixture

When the diol is water-soluble, the diol can be usually removed by repeatedly washing the mixture obtained in step (I) with water. On the other hand, when the diol is hardly water-soluble, a non-polar organic solvent, such as n-hexane, cyclohexane, benzene or toluene, in which the diol is insoluble, is appropriately selected, and the reaction mixture is diluted 2- to 10-folds with this organic solvent, and thereby the precipitated diol can be removed by filtration. However, since the (meth)acrylic acid diester obtained as a by-product has solubilities to various solvents similar to those of the (meth)acrylic acid monoester, the separation thereof from the reaction mixture by these processes is difficult. Therefore, in the subsequent process, the monoester is used as a mixture with the diester.

(III) Preparation of Phosphate Monoester

The mixture comprising the (meth)acrylic acid monoester and the (meth)acrylic acid diester is reacted with phosphorus oxychloride or pyrophosphoric acid, to prepare a phosphate monoester. In this process, the phosphate monomer can be quantitatively prepared from the (meth)acrylic acid monoester.

(IV) Isolation of Phosphate Monoester

The reaction mixture is added to a non-polar organic solvent such as n-hexane or toluene, and the (meth)acrylic acid diester, which is a by-product from step (I), is dissolved in the organic solvent, to remove it by extraction, to give a phosphate monoester having high purity. Alternatively, the phosphate monoester is extracted to an aqueous layer by forming a sodium salt or a barium salt thereof, to separate the water-insoluble (meth)acrylic acid diester, and thereafter the aqueous layer is again made acidic to recover a phosphate monoester, thereby giving a phosphate monoester having high purity.

The present applicant has manufactured the above phosphate monomers by themselves, and marketed dental materials comprising the phosphate monomers. In addition, the preparation process concretely disclosed in the above publications can be relatively easily carried out on an industrial scale, and the resulting phosphate monomers have satisfactory performance for practical purposes. However, the present inventors have pursued to further improve the following features, to provide even higher quality phosphate monomers.

1) Improvement in Yield of Phosphate Monomer (Phosphate Monoester)

The reaction mixture obtained in step (I) contains a considerable amount of the (meth)acrylic acid diester, not a desired product, in addition to the unreacted diol, and the (meth) acrylic acid monoester, essential in the subsequent preparation of the phosphate monoester. The studies of the present inventors have revealed that the ratio of monoester/diester/unreacted diol is 0.8–2/1/0.5–1.5. The formation of the (meth)acrylic acid diester merely wastes the diol, which is economically disadvantageous. Particularly when the diol is expensive, there arises a large problem in costs.

Further, in step (IV), if the amount of the (meth)acrylic acid diester admixed in the proportion to the desired phosphate monoester is large, the purity is less likely to increase when the diester is purified by extraction removal with hexane, or the like. In addition, if the purity is tried to increase, the amount of the solvent used in extraction becomes large, or the number of extraction steps repeated becomes large, so that there also arise problems in economic disadvantages and efficiency.

2) Decrease in Coloring

The phosphate monoester obtainable by the preparation process described above has satisfactorily high purity as determined by a liquid chromatography analysis. However, as the phosphate monoester is purified, the coloring ranging from pale yellow to pale brown may be observed in some cases. In a dental adhesive comprising such a colored phosphate monomer, there arise defects that it would be difficult to adjust the color tone of the adhesive to a desirable one having excellent visually acceptable appearance, and that the color of the part restored with the adhesive does not match with the surrounding teeth.

3) Improvement in Storage Stability

When a phosphate monomer per se or a dental adhesive comprising a phosphate monomer is stored for a long period of time, the viscosity thereof may increase, thereby causing gelation or solidification in some cases. Further, there arises a problem of lowering the quality for products such that the adhesive has lowered adhesion strength after gelation or solidification thereof.

Accordingly, an object of the present invention is to provide an organophosphate compound (phosphate monomer) having further improved storage stability and color tone suitability for teeth and for a restorative material of teeth, particularly useful for a dental adhesive, the organophosphate compound having a polymerizable group.

Another object of the present invention is to provide a process for efficiently preparing the phosphate monomer, specifically a (meth)acrylic acid monoester monophosphate ester, from a raw material diol.

A still another object of the present invention is to provide a dental polymerizable composition comprising the phosphate monomer.

These and other objects of the present invention will be apparent from the following description.

DISCLOSURE OF INVENTION

As a result of intensive studies, the present inventors have found that the above storage stability is associated with ionic substances contained in trace amounts in a phosphate monomer. The ionic substances may be presumably ascribed to raw materials and reagents used, impurities in a solvent, by-products, a reaction vessel, and the like. The present inventors have found a tendency that the larger the contents of these ionic substances, the more distinctively exhibited the problem associated with the storage stability. Further, when electric conductivity of the resulting phosphate monomer is measured as a method for quantifying the ionic substances admixed in the phosphate monomer, there is a distinct relationship that the larger the electric conductivity, the poorer the storage stability. Concretely, when electric conductivity of a 10% by weight methanol solution of the phosphate monomer is 0.5 mS/cm or less, more preferably 0.4 mS/cm or less, storage stability of the phosphate monomer and a dental polymerizable composition comprising the phosphate monomer is found to be excellent.

In addition, the present inventors have found a method of quantifying a level of coloring of the phosphate monomer, and recognized that the problem associated with the color tone suitability can be solved when the light transmittance of the phosphate monomer determined at 455 nm is 90% or more, more preferably 95% or more. In addition, the present inventors have further studied, and as a result, they have found that a cause of coloring of the phosphate monomer is a compound having a carbonyl group contained in a raw material diol. Moreover, they have found that when the amount of the carbonyl compound described above is 0.1% by mol or less, more preferably 0.05% by mol or less, to the raw material diol, there can be prepared a phosphate monomer with excellent color tone suitability which can be used as a raw material for a dental polymerizable composition.

Furthermore, the present inventors have studied on raw materials, intermediates, preparation conditions, washing method and the like in the preparation process, and found that an yield of the phosphate monomer, specifically a (meth)acrylic acid monoester monophosphate ester, can be improved by adding a new step to the process. Accordingly, the present invention has been perfected.

Specifically, the present invention pertains to:

[1] an organic phosphate compound having at least one radically polymerizable double bond, at least one phosphate residue having one or two hydroxyl groups, and at least one hydrocarbon group having 4 or more carbon atoms in a molecule, wherein a 10% by weight methanol solution of the organic phosphate compound has an electric conductivity at 25° C. of 0.5 mS/cm or less, and/or the organic phosphate compound has a light transmittance at 455 nm of 90% or more;

[2] a dental polymerizable composition comprising:

(a) an organic phosphate compound having at least one radically polymerizable double bond, at least one phosphate residue having one or two hydroxyl groups, and at least one hydrocarbon group having 4 or more carbon atoms in a molecule, wherein a 10% by weight methanol solution of the organic phosphate compound has an electric conductivity at 25° C. of 0.5 mS/cm or less, and/or the organic phosphate compound has a light transmittance at 455 nm of 90% or more; and (b) a polymerizable monomer capable of copolymerizing with the organic phosphate compound;

[3] a process for preparing a (meth)acrylic acid monoester monophosphate ester, comprising:

reacting 1 to 5 moles of a diol having 4 to 30 carbon atoms with 1 mole of a (meth)acrylic acid at a reaction ratio of the (meth)acrylic acid of 60 to 90% by mol, to give a reaction mixture comprising a (meth)acrylic acid monoester of the diol and a (meth)acrylic acid diester of the diol, the molar ratio of the (meth)acrylic acid monoester of the diol to the (meth)acrylic acid diester of the diol being 2 to 8; and reacting the resulting (meth)acrylic acid monoester of the diol with a phosphorus oxychloride, to give the (meth)acrylic acid monoester monophosphate ester;

[4] a process for preparing a (meth)acrylic acid ester monophosphate ester, comprising:

reacting a monohydroxy (meth)acrylic acid ester comprising one hydroxyl group, at least one (meth)acryl group, and an organic acid residue having at least one hydrocarbon group having 4 to 30 carbon atoms, with a phosphorus oxychloride in the presence of an amine compound, to give a reaction mixture comprising the (meth)acrylic acid ester monophosphate ester, a chloride of (meth)acrylic acid ester monophosphate ester, and an amine salt;
washing the reaction mixture with an acidic aqueous solution to extract out the amine salt into an aqueous layer; and
washing the resulting reaction mixture with an aqueous solution of electrolytes made acidic by hydrogen chloride formed by hydrolysis of the chloride of (meth) acrylic acid ester monophosphate ester;

[5] a process for preparing an organic phosphate compound, comprising subjecting a (meth)acrylate compound having at least one hydroxyl group as a raw material to phosphate esterification of hydroxyl group of the raw material with a phosphorus oxyhalide, wherein the (meth)acrylate compound is prepared by (meth)acrylic acid esterification of a polyol compound having an organic group having 4 or more carbon atoms and two or more hydroxyl groups in a molecule with a (meth)acrylic acid derivative while keeping at least one hydroxyl group, and wherein a content of a carbonyl compound in the polyol compound is 0.1% by mol or less; and

[6] a process for preparing a (meth)acrylic acid monoester monophosphate ester, comprising:
reacting 1 to 5 moles of a diol containing a carbonyl compound in an amount of 0.1% by mol or less, and having 4 to 30 carbon atoms with 1 mole of a (meth) acrylic acid, to give a reaction mixture comprising a (meth)acrylic acid monoester of the diol and a (meth) acrylic acid diester of the diol;
reacting the resulting (meth)acrylic acid monoester with a phosphorus oxychloride in the presence of an amine compound, to give a reaction mixture comprising the (meth)acrylic acid monoester monophosphate ester; and
washing the reaction mixture with an acidic aqueous solution and with an aqueous solution of electrolytes.

BEST MODE FOR CARRYING OUT THE INVENTION

An organophosphate compound of the present invention, namely a phosphate monomer having at least one radically polymerizable double bond, at least one phosphate residue having one or two hydroxyl groups, and at least one hydrocarbon group having 4 or more carbon atoms in a molecule, is particularly useful as an adhesive monomer. According to the studies made by the present applicant, there has been elucidated that existence of a hydrocarbon group, which has 4 or more carbon atoms, with strong hydrophobicity in a molecule greatly contributes to the adhesion to teeth and the durability.

The term "phosphate residue having one hydroxyl group" in the phosphate monomer according to the present invention refers to a structure unit:

In addition, the term "phosphate residue having two hydroxyl groups" refers to a structure unit:

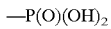

Here, each of the phosphate residues corresponds to a phosphate group and a phosphonate group.

In addition, examples of the radically polymerizable double bond referred to in the present invention include a styrene group, a cyanoacrylic group, a vinyl ether group, a (meth)acrylic group, and the like, and the (meth)acrylic group is most preferable.

The phosphate monomer according to the present invention comprises at least one hydrocarbon group having 4 or more carbon atoms in a molecule. The hydrocarbon group may be those in which hydrogen atom of the hydrocarbon group is substituted by a halogen, a hydroxyl group, a carboxyl group, a mercapto group, a cyano group, a phosphonic acid group, a phosphate group, and the like. In addition, preferable is a phosphate monomer having a structure in which the carbon atoms of the hydrocarbon group does not exceed 20 and a sum of the carbon atoms of the entire hydrocarbon groups in the molecule is within 40, from the viewpoint of ease in preparation and availability of a raw material.

The phosphate monomer preferable from the viewpoint of obtaining high adhesion includes those having a structure in which each of the hydrocarbon group having 4 or more carbon atoms, an organic group having a (meth)acrylate group and one hydroxyl group is bound with the phosphate residue. An example of such a phosphate monomer includes the following.

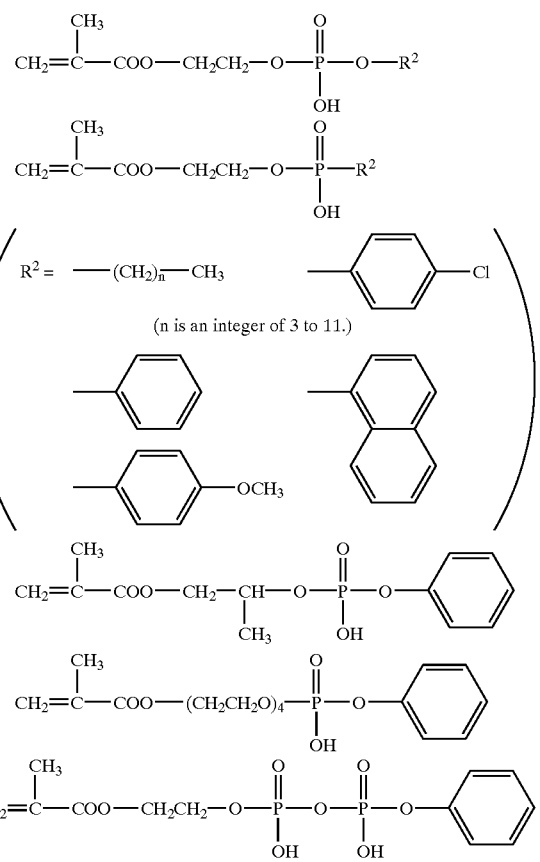

Among these phosphate monomers, those having a structure in which the hydrocarbon group bound to the phosphate residue is an aromatic group are particularly preferable.

In addition, as a different phosphate monomer exhibiting similarly high adhesion, preferable is the phosphate monomer having a structure in which the phosphate residue having one or two hydroxyl groups is bound with a (meth) acrylate group via an organic group having at least one hydrocarbon group with hydrophobicity, which has 4 or more carbon atoms, as a connecting group (spacer).

Specifically, the phosphate monomers are exemplified as follows.

The phosphate monomers are represented by the formula:

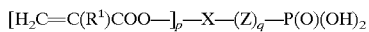

and

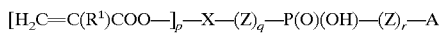

wherein $R^1$ is hydrogen atom or a methyl group; p is an integer of 1 to 4; each of q and r is 0 or 1; X is an organic group having p+1 valency, the organic group containing a hydrocarbon group having 4 or more carbon atoms; Z is oxygen atom or sulfur atom; and A is a monovalent organic residue. Examples of the organic group (spacer) represented by X are as follows.

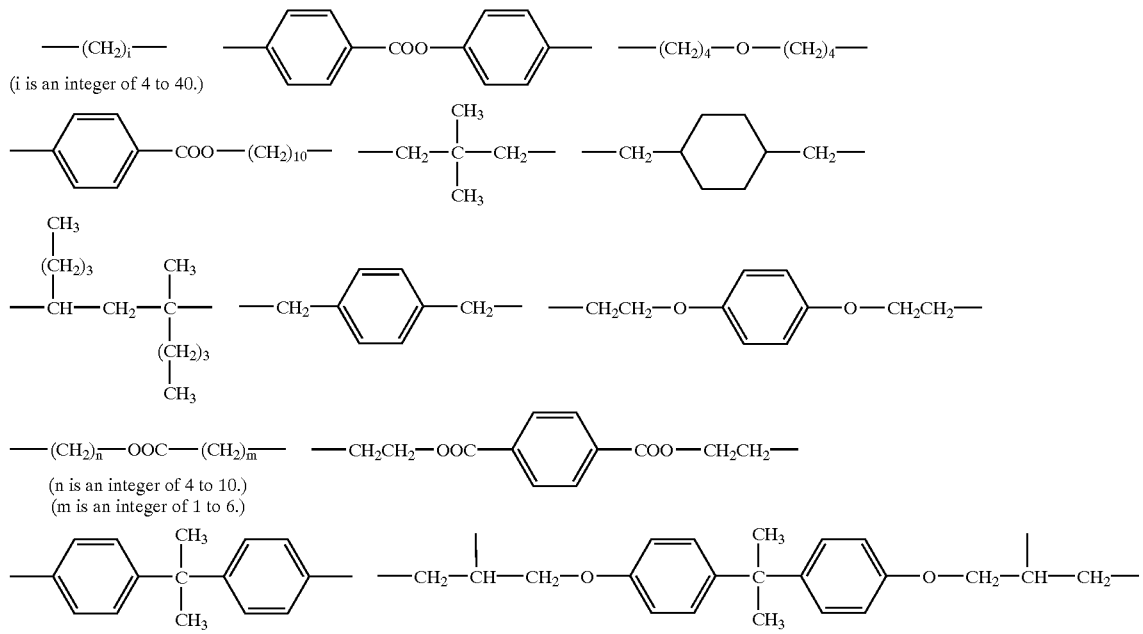

In addition, examples of the organic residue A are as follows.

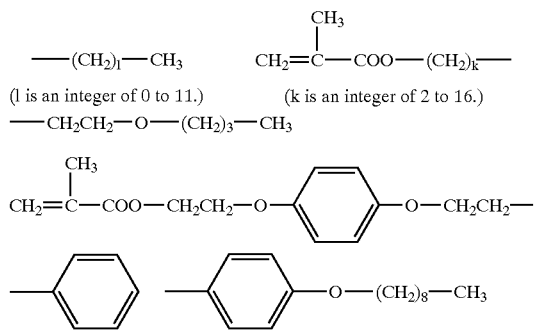

Among them, particularly preferable is a phosphate monomer having a structure in which the connecting group (spacer) is an aliphatic group having 4 or more carbon atoms, or an organic group having 8 or more carbon atoms and at least one aromatic group. These phosphate monomers have excellent penetrability to teeth at adhesion interface, thereby exhibiting particularly high adhesion.

Further, as the phosphate monomer, preferable is a phosphate monomer having a structure in which the phosphate residue having two hydroxyl groups is bound with a (meth) acrylate group via the connecting group having at least one aliphatic group having 8 to 16 carbon atoms.

The present inventors have intensively studied in view of (1) the improvement in the color tone and (2) the improvement in the storage stability of the phosphate monomer.

(1) Improvement in Color Tone of Phosphate Monomer

The phosphate monomer is colored from pale yellow to pale brown as described above. First, it has been considered that the coloring is caused by the influence of the impurities of the prepared phosphate monomer. There are several processes for preparing a phosphate monomer proposed by the present applicant. For instance, when a phosphate monoester methacryloxyalkyl dihydrogenphosphate is prepared with a hydroxyalkyl monomethacrylate from an alkyldiol such as decanediol by a process disclosed in Japanese Patent Laid-Open No. Sho. 59-139392, the purity of the desired phosphate monoester itself is from 90 to 96%, wherein the purity can be determined by NMR and HPLC analyses.

As the impurities contained in the resulting product, there are recognized by the above analyzing means a phosphate diester, a hydroxyalkyl methacrylate and an alkyldiol, which are raw materials, a dimethacrylate of an alkyldiol, a pyrophosphate derivative, methacrylic acid, and the like. However, it is found that these impurities do not affect the coloring of the phosphate monoester.

Next, the present inventors have remarked on trace amounts of impurities other than the compounds mentioned above, and further analyzed them. However, it is generally difficult to analyze the coloring-causative substance of an organic compound, which is originally colorless. This is because the coloring takes place even with a very little amount of the causative substance; the causative substance is a complicated mixture; and the stability of the causative substance itself is poor.

However, further studies have been progressed, and spectrum of the coloring is analyzed. As a result, there has been found a possibility that a compound having carbonyl group is causative of the coloring from the determination of absorbance of the phosphate monoester.

In general, carbonyl compounds contained in a trace amounts in organic substances are analyzed by a method of quantifying a carbonyl group by oxime-forming reaction in which the carbonyl compounds are treated with an aqueous hydroxylamine hydrochloride solution, which is referred to as the determination of the carbonyl value (COV) in the industrial field. The present inventors have also tried to analyze on the basis of this method. However, when this analysis is performed against a phosphate monoester, since the phosphate monoester itself has a (meth)acrylic group having a carbonyl group, determination of only the carbonyl compound causing coloring could not be taken.

As the studies have been further progressed, the present inventors have found from the above analysis method that a considerable amount of a carbonyl compound is contained in an alkyldiol, which is a raw material for the phosphate monoester and usable in the reaction described above. Moreover, it has been elucidated that there is a clear correlation between the content of the carbonyl compound in the diol and the extent of coloring of the phosphate monoester prepared from the diol. In other words, the carbonyl compound in the diol is likely to be admixed in the phosphate monoester without being removed during the preparation process.

According to the studies of the present inventors, when a diol having a low content of a carbonyl compound is used, a phosphate monomer having little coloring is obtained, so that the color tone suitability of the dental adhesive comprising such a phosphate monomer is remarkably improved. As described above, the present inventors have found for the first time the fact that the content of a carbonyl compound in a raw material diol affects an extent of coloring of the phosphate monomer obtained therefrom.

Furthermore, there have been found that the lower the content of a carbonyl compound, the less the extent of coloring of the resulting phosphate monomer, and the less the coloring change of the phosphate monomer with passage of time.

Although the causation for an increase in the coloring of the phosphate monomer with passage of time in a case where the carbonyl compound is contained in a large amount is not altogether clear, the present inventors have deduced that in the process of methacrylic acid esterification and phosphate esterification, a carbonyl compound (especially aldehyde) self-oxidizes, or is allowed to cause condensation reaction with other impurities components, thereby forming a compound with an intensive coloring which has n conjugate chromophore.

Specifically, the phosphate monomer of the present invention has a low content of a carbonyl compound, which is a causative substance for the coloring, concretely the phosphate monomer having a given level or higher level of light transmittance, when the phosphate monomer is stored at 45° C. for 14 days, and thereafter the light transmittance at 455 nm is measured. The storage of the phosphate monomer at 45° C. for 14 days is equivalent to an about two-year storage at 4° C. in a refrigerator, which can be regarded as a reasonable storage period for actual use of the phosphate monomer.

In addition, the present inventors have found that an extent of coloring of the phosphate monomer obtained in the manner described above greatly affects the color tone suitability of the dental adhesive comprising the phosphate monomer. In other words, the higher the extent of coloring of the phosphate monomer, the more the occurrence of coloring of the composition itself comprising the phosphate monomer, so that a desired color tone thereof cannot be obtained. Also, a distinct correlation has been found that the lower the light transmittance of the phosphate monomer at 455 nm, the poorer the color tone suitability.

Moreover, in order to improve the problem concerning the color tone suitability described above, they have found that the light transmittance at 455 nm of the phosphate monomer is 90% or more, more preferably 95% or more.

The light transmittance of a phosphate monomer referred to in the present invention is measured by a spectrophotometer, and the light transmittance is expressed as a proportion of intensity of the light passing through a measurement cell made of glass or silica, which is charged with a phosphate monomer without dilution, to intensity of the light passing through a vacant cell.

The light transmittance of the phosphate monomer will be further described below. The light transmittance varies in a visible light wavelength region of from 370 to 800 nm according to the extent of coloring, the extent of coloring change near 455 nm being the largest. Further, by measuring the light transmittance without dilution, the detection accuracy of the variation of the light transmittance can be made remarkably high. Incidentally, some phosphate monomers may be solid at an ambient temperature, and in such cases, a thermostat is attached in a spectrophotometer, and a cell is heated to melt the phosphate monomer. Thereafter, the measurement of the light transmittance of the phosphate monomer is taken.

(2) Improvement in Storage Stability

First, the impurities in the phosphate monomer obtained are analyzed in the same manner as in item (1) mentioned above. However, the studies of the present inventors have elucidated that the purity of the phosphate monomer and the kinds and contents of the above impurities, as determined from the results of NMR and HPLC analyses, have substantially no correlation with the present problem.

Next, the present inventors have remarked on trace amounts of impurities other than these compounds. Therefore, various analyses were performed against the resulting phosphate monomer, and as a result it has been found that a considerable amount of ionic substances is admixed in the resulting product. When analyzed by ion chromatography, there are detected ions such as $Na^+$, $SO_4^{2-}$, $Cl^-$, $PO_4^{3-}$, $NH_4^+$, $NO_3^-$ and $Fe^+$. These ions may be ascribed to raw materials and reagents used, impurities in a solvent, by-products, reaction vessels, and the like.

As a result of the progress of the studies on the effects of these ionic substances, there has been found a tendency that the larger the content of these ionic substances, the more remarkable the exhibition of the problem mentioned above. Further, when electric conductivity of the resulting phosphate monomer is determined as a method for quantifying these ionic substances admixed in the phosphate monomer, there has been found a distinct correlation that the larger the electric conductivity, the poorer the storage stability.

The studies by the present inventors have revealed that the electric conductivity of the phosphate monomer without substantially containing ionic impurities is in the range of from 0.1 to 0.2 mS/cm, and the storage stability when using a phosphate monomer having such a high purity is at a satisfactory level. However, there is found a tendency that the more the ionic substances are admixed, the higher the electric conductivity, and the poorer the storage stability. In order to improve the problem concerning the storage stability described above, the present inventors have found that it is necessary to adjust the electric conductivity of the phosphate monomer to 0.5 mS/cm or less, more preferably 0.4 mS/cm or less. The above relationship between the electric conductivity and the storage stability of the phosphate monomer is a fact found for the first time by the present inventors.

The electric conductivity of the phosphate monomer in the present invention refers to a value obtained by preparing a 10% by weight methanol solution of the resulting phosphate monomer, and thereafter determining the electric conductivity of the solution at 25° C.

In a phosphate monomer only having an organic group having 3 or less carbon atoms, there is substantially no special correlation between the electric conductivity and the problem of the storage stability addressed in the present invention, and the storage stability is excellent even though the electric conductivity is high. Such facts are also new findings by the present inventors.

Further, there is a tendency that the larger the number of carbon atoms of the organic group in a phosphate monomer, the lower the electric conductivity has to be, in order to have the same level of storage stability. For instance, in a case where the hydrocarbon group of a phosphate monomer has 4 to 7 carbon atoms, a satisfactory storage stability is obtained when the electric conductivity of the phosphate monomer is 0.5 mS/cm or less, and when the hydrocarbon group has 8 or more carbon atoms, it is desirable that the electric conductivity is 0.4 mS/cm or less.

In a phosphate monomer having a hydrocarbon group having a large number of carbon atoms, although the reason why the storage stability of the composition becomes poor when the amount of ionic substances is large are not clear at present, it is deduced as follows. When ionic substances are present, phosphate monomers are associated with each other in a solution via the ionic substances as a cross-linking site. Further, when the phosphate monomer has a hydrocarbon group with high hydrophobicity, which has a large number of carbon atoms, it is likely to easily form a molecular agglomerate structure in a very large network manner, so that the viscosity increases and the gelation accelerates.

In addition, when such a large molecular agglomerate structure is present in a dental polymerizable composition, the penetration of the phosphate monomer to dentine at the adhesion interface upon the adhesion to teeth, especially dentine tissues, becomes poor, so that the formation of a resin-immersion layer is inhibited, thereby lowering the adhesive strength.

Next, the process for preparing a phosphate monomer of the present invention will be described.

In general, several processes have been known as a process for preparing a phosphate-based monomer. For instance, the phosphate monomer is prepared by the esterification reaction of phosphoric acid or an active derivative thereof with an alcohol, or the reaction of phosphorus pentoxide with an alcohol. On the other hand, as a process for preparing a phosphate monomer of the present invention, it is desired to employ a preparation process in which the amount of a substance causative of coloring or the amount of ionic substances admixed in the resulting product is made as small as possible. From this viewpoint, there is employed a process of subjecting a compound having two or more hydroxyl groups to (meth)acrylic acid esterification with a (meth)acrylic acid derivative, the compound keeping at least one hydroxyl group; and subjecting the resulting (meth)acrylate compound having at least one hydroxyl group as a raw material to phosphate esterification of the hydroxyl group of the compound with a phosphorus oxyhalide. In this process, an especially economically advantageous and simple process is a process in which phosphorus oxychloride as a phosphorus oxyhalide is used, and phosphorus oxychloride and a (meth)acrylate compound having a hydroxyl group are reacted by adding a tertiary amine such as triethylamine as a hydrogen chloride-removing reagent.

Subsequently, water is added thereto to hydrolyze P—Cl bond to form a phosphate group, to thereby give a desired phosphate monomer. Incidentally, if the initial amount of the (meth)acrylate compound having a hydroxyl group to that of the phosphorus oxychloride is 1 mole or less, the resulting phosphate monomer mainly comprises a monoester of phosphate having a dihydrogenphosphate group, and if the initial amount of the (meth)acrylate compound is larger than 1 mole, the proportion of a diester of phosphate having a monohydrogenphosphate group increases.

In addition, in the preparation process described above, as the (meth)acrylate compound, there can be also used a monohydroxy(meth)acrylic acid ester comprising one hydroxyl group, at least one (meth)acrylic group and at least one organic residue having a hydrocarbon group of 4 to 30 carbon atoms as a raw material. The organic residue refers to a group having a structure of a hydrocarbon group which is unsubstituted or substituted by a halogen atom, or the like, wherein the hydrocarbon group may contain one or more binding units such as an ether bond, an ester bond and an amide bond.

Concrete examples of the above monohydroxy(meth)acrylic acid ester include the following:

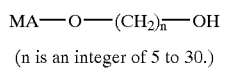

(n is an integer of 5 to 30.)

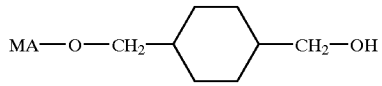

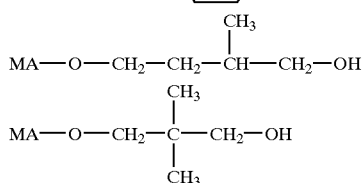

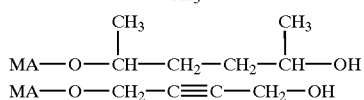

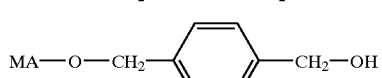

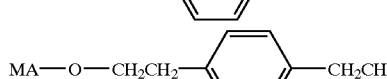

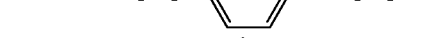

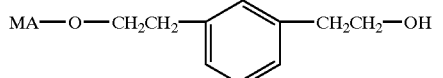

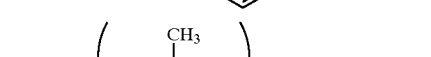

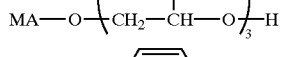

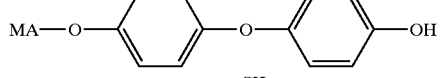

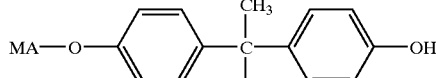

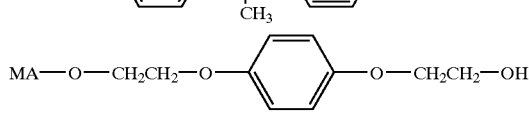

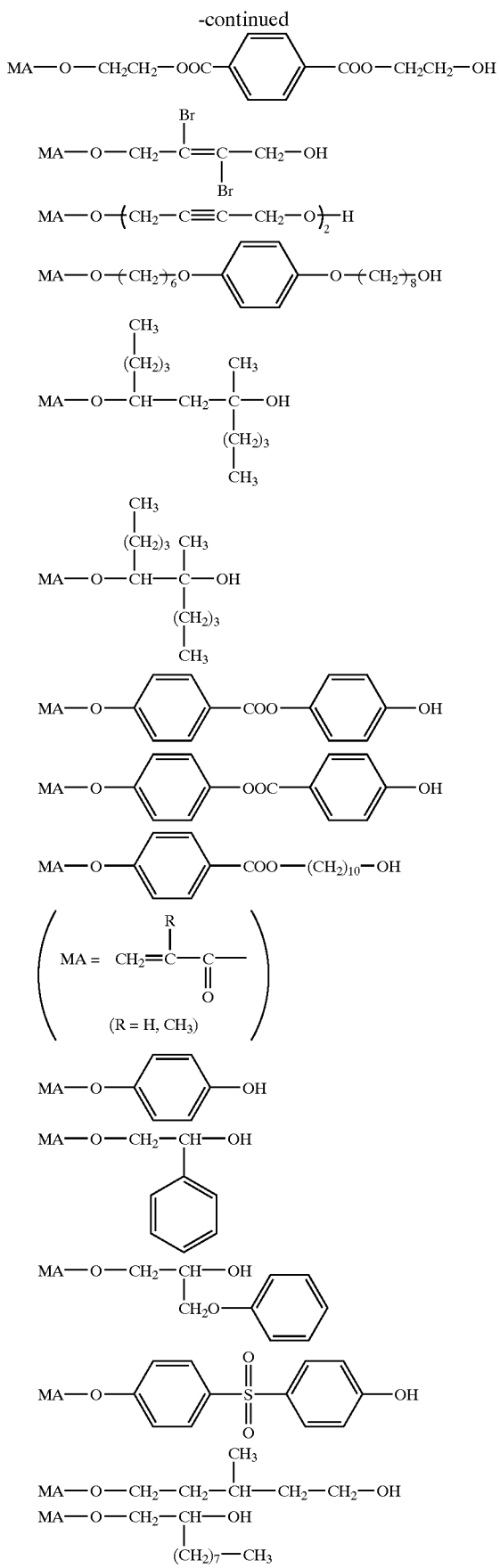

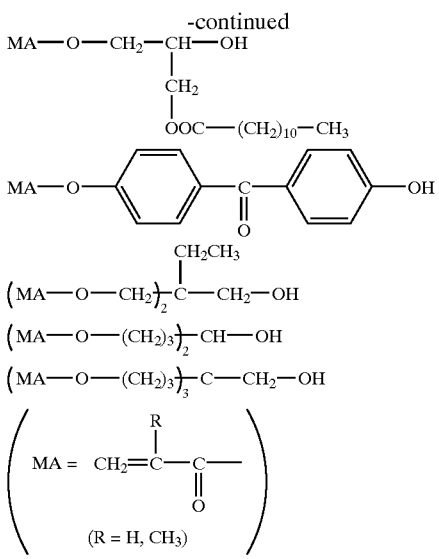

Incidentally, when the phosphate monomer according to the present invention is prepared by the process described above, there can be preferably used, as a compound having two or more hydroxyl groups, a polyol compound having an organic group having 4 or more carbon atoms and two or more hydroxyl groups in the molecule, especially a diol having 4 to 30 carbon atoms. A diol having 5 to 30 carbon atoms is preferably used. In addition, among the phosphate monomers obtained by the process described above in such a case, a phosphate monoester is preferable. Incidentally, the structure of the diol other than two hydroxyl groups thereof may have a hydrocarbon group which is unsubstituted or substituted by a halogen atom, or the like, wherein the hydrocarbon group may contain one or more binding units such as an ether bond, an ester bond and an amide bond, with proviso that two hydroxyl groups of the diol is not directly bound with these binding units.

Concrete examples of the diols are the following.

(n is an integer of 5 to 30.)

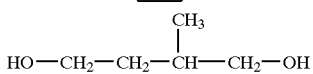

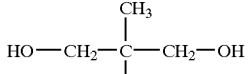

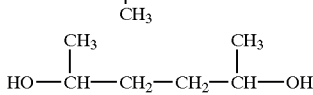

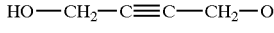

-continued

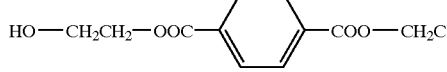

-continued

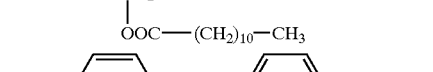

Among the diols, a phosphate monoester prepared from a compound:

HO—(CH$_2$)$_n$—OH n=9 to 16 can be suitably used as a raw material for a dental polymerizable composition having excellent adhesive strength and high level of water resistance.

Also, if a phosphate monoester is prepared using the diol, the difference in the solubilities between the desired phosphate monoester and the (meth)acrylic acid diester to be removed is large in a nonpolar solvent such as hexane used for the extraction process in the purification process of step (IV), so that only the (meth)acrylic acid diester can be readily dissolved into hexane, to easily remove the diester from the reaction mixture. Therefore, the use of the diol is preferable.

As a means for obtaining a phosphate monomer having high light transmittance with preventing admixture of substances causative of the coloring in the process described above, there is a process where raw materials, reagents, solvents and the like having high purities are selected for use. In this aspect, as previously described, a process using a compound having two or more hydroxyl groups, which contains a carbonyl compound as an impurity in as low an amount as possible, when subjecting the compound having two or more hydroxyl groups to methacrylic acid esterification reaction is especially useful.

The carbonyl compound contained in a compound having a hydroxyl group is detected by the following method. Specifically, when a solution prepared by diluting a raw material diol with an appropriate solvent is treated with an aqueous hydroxylamine hydrochloride solution, those having a carbonyl group among the impurities contained in the raw material diol liberate an equimolar hydrochloric acid to the carbonyl group by the oxime-formation reaction, and the liberated hydrochloric acid is subjected to neutralization titration with an alcoholic potassium hydroxide solution, and the number of carbonyl groups is obtained by converting the amount of potassium hydroxide consumed in the titration. This process is employed as a method for measuring carbonyl value (COV) in the industrial field. According to the studies by the present inventors, when measured by this method, the amount of carbonyl compounds in the polyol compound such as raw material diol, as expressed as the number of carbonyl groups to the polyol compound, is concretely preferably 0.1% by mole or less, more preferably 0.05% by mole or less.

In addition, as a means for preventing admixture of ionic substances, reagents used such as phosphorus oxychloride o r amine are not to be used in excess in the proportion to a raw material (meth)acrylate having hydroxyl group, besides selecting raw materials, reagents, solvents and the like having high purities for use. The excessive addition gives rise to causes for remaining phosphate ions and amine hydrochloride.

The process for preparing a phosphate monomer of the present invention, especially the process for preparing a phosphate monoester, will be concretely explained for each process, taking an example of using a diol as the polyol compound.

(A) Preparation of (Meth)acrylic Acid Monoester

A (meth)acrylic acid monoester is prepared by carrying out esterification reaction of a (meth)acrylic acid and a diol at 130° C. or less in absence of a solvent or in an inert solvent such as benzene, toluene or a halogenated benzene, in the presence of an acid catalyst. The molar ratio of the (meth)acrylic acid monoester of the diol/(meth)acrylic acid diester of the diol in the resulting reaction mixture is preferably adjusted to 2 to 8, from the viewpoint of improving the yield of the phosphate monoester to be obtained finally. When the initial amount of the diol is very small in the proportion to the (meth)acrylic acid, the (meth)acrylic acid diester which is unnecessary at the final stage is likely to be formed, so that the molar ratio of the monoester/diester in the resulting (meth)acrylic acid ester mixture is undesirably likely to be 2 or less. Therefore, it is desired that the initial amount of the diol is 1 to 5 moles, preferably 1 to 3 moles, per one mole of the (meth)acrylic acid.

As the acid catalyst, there may be employed a strong acid such as sulfuric acid, sulfonic acid or phosphoric acid, and the acid catalyst is added in an amount of 0.1% to 15% by weight to the entire initial amounts of raw materials. In addition, in order to inhibit polymerization during esterification reaction, there may be added a polymerization inhibitor or suppressor such as hydroquinone monomethyl ether (abbreviated: MEHQ), hydroquinone and 2,6-di-tert-butyl-p-cresol (abbreviated: BHT), in an amount of 50 to 10000 ppm to the (meth)acrylic acid. Further, the polymerization inhibition is also achieved by blowing air or oxygen into a reaction mixture, but there is still a risk of polymerization when the reaction temperature exceeds 130° C. Therefore, it is preferable that the reaction is carried out at 130° C. or lower, preferably 100° C. or lower. In addition, the reaction may be carried out at ambient pressure, and it may be also carried out under reduced pressure in order to quicken the progress of the reaction by promoting the removal of formed water by distillation.

The mixture during the reaction is sequentially monitored by using analyzing means such as liquid chromatography or gas chromatography. The formation of the (meth)acrylic acid monoester and diester initiates at the same time as the initiation of the reaction, and the formation rate of the monoester is fast in the beginning stage of the reaction, and the formation rate of the diester, on the other hand, rather quickens as the reaction progresses. As a result of the studies, the present inventors have found that when the (meth)acrylic acid added initially is used for the reaction in the proportion of from 60 to 90%, further preferably from 75 to 90%, an increase in the monoester stops, so that an increase in the diester becomes the main reaction thereafter.

By stopping the reaction at this stage, the (meth)acrylic acid monoester, essential in the preparation of a phosphate monoester, can be obtained at a high yield to an unnecessary (meth)acrylic acid diester, wherein the ratio of (meth)acrylic acid monoester/(meth)acrylic acid diester is from 2 to 8 as a molar formation ratio.

An unreacted diol is removed in accordance with step (II) from an organic solvent containing the reaction mixture. This unreacted diol can be recovered to be reused. The organic layer obtained by removing the aqueous layer may be optionally subjected to decolorizing treatment with activated charcoal. Further, simultaneously with the decolorizing treatment, sodium sulfate, magnesium sulfate, molecular sieves, and the like may be added to also carry out dehydration procedures.

Thereafter, the decolorizing agent, the desiccant and the solvents are removed, to give a mixture comprising the (meth)acrylic acid monoester and diester of the diol.

The (meth)acrylic acid monoester may be also prepared by transesterification reaction of a diol and a methyl (meth) acrylate or HCl-removing condensation of a diol and a (meth)acrylic acid chloride, as well as by esterification reaction of a diol and a (meth)acrylic acid. The object of the present invention can be similarly achieved by reacting the diol in an amount of 1 to 5 moles per one mole of the methyl (meth)acrylate or the (meth)acrylic acid chloride, and adjusting a reaction ratio of the methyl (meth)acrylate or the (meth)acrylic acid chloride to 60 to 90%.

(B) Preparation of Phosphate Monoester

The unreacted dial is recovered, and thereafter a hydroxyl group of the (meth)acrylic acid monoester is subjected to phosphate esterification. Although any of known techniques which are numerously known, may be basically utilized, there is the following process utilizing phosphorus oxychloride as a simple process with high yield. This process can be considered to be divided into the following two steps (i) and (ii).

(i) Preparation of Compound having —P(O)Cl$_2$ Group (First Dropping Step of Amine)

The reaction process is represented by the following chemical equation (m).

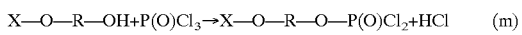

X—O—R—OH+P(O)Cl$_3$→X—O—R—O—P(O)Cl$_2$+HCl　　(m)

wherein X—O—R—OH is a (meth)acrylic acid monoester; X is a (meth)acroyl group; and R is an organic residue having 4 to 30 carbon atoms.

As shown in the chemical equation (m), the (meth)acrylic acid monoester is reacted with phosphorus oxychloride. As the (meth)acrylic acid monoester, it is preferable to use those having high purity, and it may be subjected to reaction as a mixture with the (meth)acrylic acid diester prepared in (A) described above. When the reaction is carried out at 0° C. or more, the phosphate diester is likely to be formed as a by-product, and when the reaction is carried out at −60° C. or less, the reaction rate is drastically slowed. Therefore, the reaction is carried out at preferably from −60° to 0° C., more preferably from −50° to −10° C.

In addition, in this reaction, in order to recover the formed hydrogen chloride, an amine compound is added as a reaction aid. The amine compound is preferably a tertiary amine such as triethylamine, tributylamine or pyridine, from the viewpoint of easily forming hydrochloride owing to its strong basicity. In particular, triethylamine is more preferably used from the viewpoint of easy removal during purification.

When the phosphorus oxychloride and the amine compound are used in exceedingly large amounts, ionic substances increase, thereby leading to occurrence of poor storage stability of a phosphate monoester, the final product, as described above. Therefore, it is preferable that the amount of each of the phosphorus oxychloride used and the amine compound used is equimolar or in slight excess to one mole of the (meth)acrylic acid monoester.

Concretely, 1 to 2 moles of phosphorus oxychloride and 1 to 1.2 moles of the amine compound, preferably triethylamine, are reacted to the mixture of the monoester and diester of (meth)acrylic acid prepared above per one mole of the monoester in the mixture at a temperature of −60° to 0° C.

The phosphorus oxychloride is diluted with a solvent such as ethyl ether, tetrahydrofuran, 1,4-dioxane, ethyl acetate, dichloromethane, chloroform and benzene, and preferably kept at a temperature of −50° to −10° ° C. The (meth)acrylic acid monoester and the amine compound may be used without dilution or by appropriately diluting with a solvent such as an ether, and added to the phosphorus oxychloride. At this point, the (meth)acrylic acid monoester and the amine compound may be added in that order, or they may be previously mixed, and then added. In addition, after the addition, the reaction mixture is kept at −50° to −10° C. and continued stirring for 30 to 60 minutes.

At this stage, a chloride of a phosphate monoester having —P(O)Cl$_2$ group shown in the chemical equation (m) is formed.

(ii) Preparation of Phosphate Monoester by Hydrolysis of Chloride of Phosphate Monoester
(Second Dropping Step of Amine)

The reaction process is represented by the following chemical equation (n).

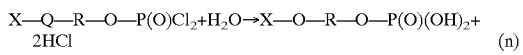

$$\text{X—Q—R—O—P(O)Cl}_2 + \text{H}_2\text{O} \rightarrow \text{X—O—R—O—P(O)(OH)}_2 + 2\text{HCl} \qquad (n)$$

wherein X and R are as defined in the chemical equation (m).

As shown in the chemical equation (n), the chloride of a phosphate monoester is allowed to hydrolyze to prepare a phosphate monoester. In this step, in order to smoothly progress the reaction, the reaction temperature is elevated to be higher than that of First Dropping Step of Amine. However, since the reaction products cannot be controlled if the reaction temperature is too high, the reaction temperature is preferably 20° C. or less, more preferably from 0° to 10° C. Water is added in excess to phosphorus oxychloride, but when the amount of water is extremely large, the resulting reaction mixture is undesirably likely to be inhomogeneous. Therefore, it is preferable that water is added in an amount of 3 to 30 moles or so.

Also in this reaction, an amine compound is added in order to recover the formed hydrogen chloride. It is preferable to use triethylamine as the amine compound for the same reasons given in the reaction of (i) above. The amine compound is added so that an entire amine amount of First Dropping and Second Dropping Steps is from 2.5 to 2.9 moles per one mole of phosphorus oxychloride. In addition, water and the amine compound may be added in that order, or a liquid mixture of water and the amine compound may be added dropwise.

In this stage, a desired product phosphate monoester is formed, and an amine salt formed by reaction with hydrogen chloride as a by-product is also contained in the reaction mixture. In addition, when the (meth)acrylic acid monoester in First Dropping Step of Amine is subjected to the reaction as a mixture with the (meth)acrylic acid diester, the (meth) acrylic acid diester is also admixed as an impurity. Further, since an entire amount of the amine is adjusted to an amount less than the stoichiometric amount (3-folds by mole of the phosphorus oxychloride), a trace amount of an unreacted chloride of a phosphate monoester remains in the reaction mixture.

Incidentally, in a case, for instance, where a phosphate monomer is prepared according to the above process with the monohydroxy(meth)acrylic acid ester exemplified above and the like, a (meth)acrylic acid ester moiety is not necessarily one in the desired product, in which case the product is a (meth)acrylic acid ester monophosphate ester, and a trace amount of an unreacted chloride of a (meth)acrylic acid ester monophosphate ester remains in the reaction mixture as in the case of the phosphate monoester described above.

As a result of intensive studies, the present inventors have found that when a purification process for removing the amine salt in the manner described below in the presence of a trace amount of the chloride of a phosphate monoester is carried out, the formation of ionic substances can be suppressed, thereby giving a phosphate monoester having excellent storage stability. Incidentally, when the product is the (meth)acrylic acid ester monophosphate ester, the same purification procedures may be employed.

(C) Purification Process of Phosphate Monoester

In the reaction mixture obtained in steps (i) and (ii), ionic substances such as salts formed from a phosphate monoester and an alkali metal or an amine, an amine hydrochloride, hydrochloric acid and phosphoric acid are contained, and particularly it is found that the salt of the phosphate monoester is present in the largest amount.

When the ionic substances are removed, the amine salts which precipitate with the progress of the reaction can be removed by filtration after hydrolysis, and there may be also employed purification and isolation by column chromatography using silica gel or the like as a carrier, or a process of treating with an adsorbent such as activated charcoal or molecular sieves. By repeating these purification procedures or using them in combination, the ionic substances are quickly removed so that the electric conductivity of the reaction mixture can be adjusted to 0.5 mS/cm or less. However, the simplest and most economically advantageous process for removing ionic substances from a reaction mixture containing large amounts of the ionic substances is a process comprising washing the reaction mixture with water to remove the ionic substances to an aqueous layer by extraction. For instance, a general process comprises dissolving a phosphate monoester in an organic solvent such as an ether or toluene, stirring and shaking the resulting solution together with distilled water, thereby removing the ionic substances to an aqueous layer by extraction. In addition, as a similar process, there is a process comprising stirring and dispersing a reaction mixture with a great excess of water for a long period of time, and adding an organic solvent to the resulting suspension, thereby extracting only a phosphate monoester to an organic layer. As described above, when the ionic substances are removed by extraction with water, it is highly effective that a similar extraction procedure is carried out with an aqueous solution of a strong acid at a low concentration, and thereafter washing with distilled water. This is deducibly because cations in the phosphate monoester are incorporated as a salt of phosphate group of a phosphate monoester, and the cations are dissociated by adding a strong acid and likely to be easily transferred to an aqueous layer. However, in this process, the used strong acid needs to be sufficiently removed in the subsequent process. When an acid which is gaseous at an ambient temperature, such as hydrochloric acid, is used, hydrochloric acid can be also removed when an organic solvent is removed by distillation under reduced pressure.

However, according to the above process, although there may be carried out a process comprising washing a reaction mixture with an aqueous acid solution to remove an amine salt to an aqueous layer by extraction, thereby isolating a phosphate monoester to an organic layer [when a (meth) acrylic acid diester is present the diester is similarly migrated to the organic layer]; and thereafter washing the organic layer with an aqueous solvent to remove the ionic substances contained in the added acid and the reaction mixture, it has been difficult to allow layer separation of the reaction mixture because the reaction mixture becomes turbid in white (near emulsion state) at the final stage.

The present inventors have found that when washing a reaction mixture with an aqueous solvent is carried out by washing with an aqueous solution of electrolytes such as a salt solution, the reaction mixture is allowed to readily cause layer separation, thereby enabling to wash the organic layer. As a result of further studies, the present inventors have found that cations of the electrolytes in the aqueous solution of electrolytes migrate to the organic layer containing the phosphate monoester, thereby forming ionic substances.

This ionic substance comprises as a main component a salt (hereinafter referred to as "salt of a phosphate monoester") comprising a phosphate monomer and cations of electrolytes, and such a salt gives rise to an increase in the electric conductivity of the final product phosphate monoester, thereby causing poor storage stability as described above. As a result of intensive studies, the present inventors have found that when a pH of the reaction mixture during washing with an aqueous solution of electrolytes is 3.0 or less, preferably 1.5 or less, it would be difficult to form a salt of a phosphate monoester, and that as such means it is effective to have some of the chlorides of a phosphate monoester remaining without hydrolyzing all the chlorides of a phosphate monoester in Second Dropping Step of Amine as described above. In this principle, the present inventors have found that a pH of the reaction mixture is lowered by the hydrogen chloride formed by hydrolysis of the chloride of a phosphate monoester during washing, so that incorporation of cations is controlled, thereby preventing formation of a salt of a phosphate monoester. Alternatively, a different acid may be added to decrease a pH of the reaction mixture, but ionic substances undesirably increase. In addition, since the hydrogen chloride formed by this process is very small amount, it is found that there would be no problem if remained in the desired product.

The present inventors have found that the formation of the ionic substances is lowered by washing with an aqueous solution of an acid and electrolytes as described above, so that the amine salt can be removed by extraction. However, when the concentration of the washing liquid is too high, the acid and the electrolytes tend to remain in the extract, thereby causing an increase in the ionic substances. In addition, since the phosphate monoester is likely to be hydrolyzed in water, particularly an aqueous solution of an acid, the aqueous solution of an acid such as hydrochloric acid is preferably used at 0.1 to 2.0 N, and an aqueous solution of electrolytes, such as brine, is preferably used at a concentration of 0.1 to 5% by weight. In addition, when the number of wash is small, the washing is insufficient, and when the number of wash is too large, an increase in the ionic substances is likely to be caused. Therefore, the washing is preferably carried out twice or thrice.

In addition, the remaining chloride of a phosphate monoester is considered to be converted to a phosphate monoester of which entire amount is substantially hydrolyzed in the washing step with aqueous solutions of an acid and electrolytes. However, when the chloride of a phosphate monoester remains, the process may further comprise a step of hydrolyzing with water. Incidentally, in the hydrolysis employed at this stage, an amine is not used in order to omit the purification step described above.

After the washing step with the aqueous solutions of an acid and electrolytes, decolorizing treatment may be optionally carried out such that the reaction mixture is subjected to purification and isolation by column chromatography with a silica gel or the like as a carrier, or subjected to treatment with an adsorbent such as activated charcoal and molecular sieves. By repeating these purification procedures or using them in combination, the light transmittance at 455 nm of the purified product can be adjusted to 90% or more. In addition, when a (meth)acrylic acid diester is contained in the final product phosphate monoester, a phosphate monoester having high purity is obtained by removing the (meth)acrylic acid diester according to step (IV) described above.

After the final product phosphate monoester is obtained, an organic solvent is removed by distillation. During removal by distillation, a polymerization inhibitor such as BHT is added as occasion demands. The removal by distillation may be carried out by any means such as heating, reduced pressure, or a combination of heating and reduced pressure, and it is preferable to remove the solvent by distillation under reduced pressure at an ambient temperature, from the viewpoint of efficiently removing the solvent by distillation with suppressing the decomposition of the phosphate monoester. In addition, by removing the solvent by distillation at the final stage of the removal by distillation with keeping reduced pressure at 40° to 60° C., the hydrogen chloride formed as a by-product by hydrolysis can be removed in a short period of time.

In addition, the moisture of a phosphate monoester is removed by drying the product obtained under reduced pressure after removal of the solvent by distillation or by introducing a dry air to the product. A general dehydration procedure is carried out by supplying sodium sulfate, magnesium sulfate, molecular sieves, or the like, prior to removal of the solvent by distillation. However, this procedure is not desirable, because the present inventors found that when these desiccants are used at the stage of preparing the phosphate monoester, there causes the formation of ionic substances.

The process for preparing a phosphate monoester according to the present invention yields a higher product rate of a (meth)acrylic acid monoester required for the preparation of the phosphate monoester than that of a conventional process, so that the product rate of an unnecessary (meth) acrylic acid diester is lowered. When the amount of a diol used for reaction is reduced, an unreacted diol may be recovered and the diol may be reused repeatedly, thereby improving a yield of a phosphate monoester formed from the diol added in the first reaction. It is industrially effective to repeat a cycle comprising subjecting the recovered diol to (meth)acrylic acid esterification several times, and collecting a mixture comprising a monoester and a diester obtained after each repetition to be used for the subsequent phosphate esterification.

In addition, in step (IV) comprising removing a (meth) acrylic acid diester to isolate a phosphate monoester, when the reaction mixture is purified by removing the diester by extraction with, for instance, hexane or the like, the amount of a solvent used for extraction and the number of extractions can be reduced, so that a phosphate monoester having high purity can be obtained very economically advantageously and efficiently.

The phosphate monomer of the present invention is useful for an adhesive composition, especially as a main ingredient of a dental polymerizable composition. The phosphate monomer may be used alone as a dental adhesive primer or a dental adhesive, or it may be used as a dental polymerizable composition prepared by mixing the phosphate monomer and a polymerizable monomer capable of copolymerizing with the phosphate monomer, in order to adjust the viscosity, improve the mechanical strength of a cured product, and regulate other physical properties. In addition, the phosphate monomer can be also used for other dental material which is expected to have functions of both a phosphate residue and a polymerizable group. Further, the phosphate monomer can be used as an ingredient for various industrial adhesives.

The polymerizable monomer may be a known one without particular limitation, and usually a (meth)acrylate-based monomer is preferably used. Preferred examples of the (meth)acrylate-based monomer include monofunctional (meth)acrylates such as methyl (meth)acrylate, 2-hydroxyethyl (meth)acrylate, (meth)acrylic acid and 4-(meth)acryloyloxyethoxycarbonyl phthalic anhydride; bifunctional (meth)acrylates such as triethylene glycol di(meth)acrylate, 1,6-hexanediol di(meth)acrylate, bisphenol A glycidyl di(meth)acrylate (generally referred to as "Bis-GMA") and 2 moles of 2-hydroxyethyl (meth)acrylate adduct of 2,2,4-trimethylhexamethylene diisocyanate (generally referred to as "UDMA"); trifunctional (meth) acrylates such as trimethylolmethane tri(meth)acrylate; and tetrafunctional (meth)acrylates such as 2 moles of glycerol di(meth)acrylate adduct of 2,2,4-trimethylhexamethylene diisocyanate.

In the dental polymerizable composition of the present invention, a known polymerization initiator may be further added in accordance with its purposes. For instance, such an initiator includes a heat-polymerization catalyst such as benzoyl peroxide, especially when the ambient-temperature polymerization (chemical polymerization) is carried out, redox systems such as benzoyl peroxide/amine system and an organosulfinic acid (or a salt thereof)/amine/peroxide system can be preferably used.

In addition, a photopolymerization catalyst includes, for instance, α-diketone/reducing agent systems, or ultraviolet polymerization catalysts such as benzyl dimethyl ketal and acyl phosphite oxide.

On the other hand, there can be also provided a dental polymerizable composition without containing a polymerization initiator. For instance, in a method of treatment comprising applying the polymerizable composition of the present invention as a primer to a cavity surface formed by removing dental caries, packing a composite resin thereon in the cavity, and polymerizing and curing the composite resin, even if the polymerization initiator were not contained in the polymerizable composition, the polymerizable composition is polymerized and cured, thereby exhibiting an adhesion function thereof, by allowing a polymerization initiator contained in the composite resin or radicals formed during polymerization of the composite resin to migrate to the composition layer.

The application of the dental polymerizable composition comprising the phosphate monomer of the present invention includes dental adhesive primers, dental adhesives, dental cement, pit and fissure sealant, dental composite resins, resins for denture base, and the like.

An example of the dental adhesive includes a liquid polymerizable composition comprising the phosphate monomer according to the present invention, a (meth) acrylate-based monomer, and a known polymerization initiator. A homogenous composition comprising water and a hydrophilic (meth)acrylate-based monomer is especially useful for a self-etching primer exhibiting excellent adhesion to the dentine tissues.

In addition, when the dental adhesive is used as a dental composite or cement, a composition comprising a monomer composition comprising the phosphate monomer of the present invention and a filler is preferable.

The filler includes inorganic fillers such as silica, glass comprising silica as a main component, such as barium boroaluminosilicate glass, strontium boroaluminosilicate glass and fluoroaluminosilicate glass, and alumina; powder of organic compounds such as polymethyl methacrylates; organic-inorganic composite fillers, and the like.

In such compositions, a pasty composition prepared by previously mixing the monomer composition (liquid) and the filler (powder) may be provided, or alternatively, an oxidizing agent and a reducing agent are added to each of the filler and the monomer composition, and the filler and the monomer composition are well mixed just prior to use to activate the catalyst for chemical polymerization.

The dental polymerizable composition using the phosphate monomer of the present invention may further comprise a solvent, a polymerization inhibitor, an ultraviolet absorbent, a coloring agent, an antibacterial agent., and the like as occasion demands. In addition, aside from dental applications, the composition comprising the phosphate monomer of the present invention is useful for bone cement, architectural adhesives, chinaware adhesives, sealants, and the like.

The present invention will be explained by the following working examples, without intending to limit the scope or spirit of the present invention thereto. Here, the methods for measuring various properties in the working examples are collectively shown below. In the working examples and comparative examples, the diol compound and amine compound used are referred to as only "diol" and "amine," where necessary.

(1) Measurement of Electric Conductivity

Methanol (Wako Pure Chemical, Special Grade Chemical) was added to 1 g of a phosphate monoester to prepare a 10% by weight dilution. With keeping the dilution at 25° C., the electric conductivity was measured. As to the measurement device, a digital electric conductmetric device "Model CM-117" (manufactured by Kyoto Denshi Kogyo) was used.

(2) Light Transmittance of Phosphate Monoester

An appropriate amount of a phosphate monoester stored at 45° C. for 14 days was placed in a glass cell for spectrophotometer having an optical path of 10 mm, and light transmittance (%) at 455 nm was measured at 25° C. by a visible-ultraviolet spectrophotometer "Model UV-2400" (manufactured by Shimadzu Corporation).

(3) Quantitation of Carbonyl Compound in Diol (Carbonyl Value)

Forty grams of a diol was accurately measured, and the diol was added to 160 ml of a mixed solvent of toluene and neutral ethanol (volume ratio of toluene:neutral ethanol =1:1), and dissolved with stirring. Ten milliliters of a 5 wt/v % hydroxylamine hydrochloride solution was added to this solution. After the mixture was allowed to stand for one hour, titration was carried out with 1/10 N alcoholic KOH by using a potentiometric automatic titrator "Model AT-410" (manufactured by Kyoto Denshi Kogyo), and the molar ratio (%) as the number of carbonyl groups to the diol was calculated by the following equation.

Molar Ratio of Carbonyl Compounds (as Number of Carbonyl $$\text{Groups) to Diol (\%)} = \frac{[(A-B) \times f \times M]}{(100 \times S)}$$

wherein
- A is a titer of a sample (ml);
- B is a titer of the blank (ml);
- S is an amount of the sample collected;
- M is a molecular weight of a diol; and
- f is a factor of 1/10 N alcoholic KOH.

(4) Evaluation of Color Tone Suitability of Dental Adhesive

A cured product of composite resin for dental filler "CLEARFIL AP-X" (manufactured by Kuraray Co., Ltd.) having a cavity of 150 μm in width (hereinafter referred to as "resin cured product") was prepared, and a dental adhesive comprising a phosphate monoester was packed in the cavity of the dental resin cured product mentioned above. Irradiation was carried out for 10 seconds using a dental visible light irradiation device "LIGHTEL II" (manufactured by Ushio Electric) over the cavity to cure the dental adhesive. The color tone suitability was evaluated in two ranks of excellent and poor by whether or not the cured product of the dental adhesive was visibly outstanding against the resin cured product in about 1000 Lx under fluorescent lamp.

(5) Number of Days for Gelation of Dental Adhesive

Five grams of a dental adhesive comprising a phosphate monoester was placed in a glass bottle, and stored under indoor environmental conditions at 25° C. for daily observation. Gel-like, transparent impurities were precipitated as fine particles with the passage of time, and the point at which such an insoluble product was visibly observed was referred to as the number of days for gelation.

(6) Measurement of Adhesive Strength to Dentine

An ethanol solution having the following composition was prepared.

| Components | Parts by Weight |
| --- | --- |
| Ethanol | 100 |
| N,N-Diethanol-p-toluidine | 2 |
| Sodium benzenesulfinate | 4 |

A tap e with a hole of 3 mm in diameter was adhered to the bovine tooth dentine surface abraded with #1000 abrasive paper under pouring water to set an adhesive surface. A 40% aqueous phosphoric acid solution was applied to the adhesive surface, and the adhesive surface was allowed to stand for 20 seconds, and thereafter water-rinsed A dental adhesive comprising a phosphate monoester and the above ethanol solution were mixed in an equal volume, and the mixture was applied onto the adhesive surface, and shortly air-blowed with a dental air syringe.

Photopolymerization was carried out by irradiating visible light for 20 seconds using the LIGHTEL II. A dental composite resin "AP-X" was laminated thereon in a thickness of 1 mm, and photo-cured by irradiating visible light for 40 seconds using the LIGHTEL II. A stainless rod was bonded on the cured composite resin surface with a dental adhesive cement "PANAVIA 21" (manufactured by Kuraray Co., Ltd.) to prepare an adhesive test specimen. The adhesive test specimen was immersed in water at 37° C. for 24 hours, and thereafter adhesive strength was measured by using an INSTRON universal testing instrument (cross head speed at 2 mm/min). The value for the adhesive strength is an average of five test specimens.

EXAMPLE 1-1

Preparation of 10-Methacryloyloxydecyl dihydrogenphosphate (MDP)

A separable flask fitted with a mechanical stirrer and a dropping funnel was charged with a mixed solution of 18.4 g (0.12 mole) of phosphorus oxychloride in 100 ml of diethyl ether, and the mixed solution was cooled to −40° to −30° C. (internal temperature). A mixed solution of 24.2 g (0.1 mole) of 10-hydroxydecyl methacrylate and 12.1 g (0.12 mole) of triethylamine in 100 ml of diethyl ether was placed in the dropping funnel, and added dropwise with stirring to the above cooled mixed solution over a period of one hour (First Dropping Step).

The internal temperature was raised to 0° C., with stirring the reaction mixture for one hour, and a mixed solution of 6.3 g (0.35 mole) of distilled water and 20.2 g (0.2 mole) of triethylamine was further added dropwise with stirring (Second Dropping Step). After the dropwise addition, the reaction mixture was stirred for additional 2 hours, and the precipitated hydrochloride of triethylamine was separated by filtration with a glass filter. The filtrate (organic layer) was washed twice with water, and once with 1% salt solution.

After separation of the organic layer, 100 mg of hydroquinone monomethyl ether was added as a polymerization inhibitor, and thereafter the ether was distilled off under reduced pressure, to give an oily product. One-hundred grams of n-hexane was added to the oily product to wash the oily product. Thereafter, hexane dissolved in a hexane-insoluble component was distilled off under reduced pressure, to give 25 g of a desired phosphate monoester (10-Methacryloyloxydecyl dihydrogenphosphate, hereinafter simply referred to as MDP).

The oily product was analyzed by HPLC [column: CAPCELL PAK C18-SG120, mobile phase: water/methanol=2/8 (containing 0.005 M phosphoric acid), detection wavelength: 254 nm]. The purity of MDP was 93.5%.

Methanol (Wako Pure Chemical, Special Grade Chemical) was added to 1 g of the MDP to prepare a 10% by weight dilution. With keeping the dilution at 25° C., the electric conductivity was measured and found to be 0.308 mS/cm.

EXAMPLES 1-2 TO 1-4

Comparative Examples 1-1 to 1-3

The same procedures as in Example 1-1 were carried out to prepare MDP, except for using each of phosphorus oxychloride and triethylamine in amounts shown in Table 1, which were the same as those used in First Dropping Step and Second Dropping Step described above. The purity as determined by HPLC and the electric conductivity for each of the resulting MDPs are summarized in Table 1.

EXAMPLE 1-5

Two-hundred milliliters of distilled water was added to 10 g of the MDP having a high electric conductivity, which was obtained in the method of Comparative Example 1-1, and the mixture was vigorously stirred, to give a colloidal suspension. After stirring this suspension at room temperature for 10 hours, diethyl ether was added to the resulting suspension to extract the MDP into an ether layer. The ether was distilled off under reduced pressure, and about 9 g of MDP was recovered. This procedure was repeated twice to remove ionic substances, and as a result, the MDP having an electric conductivity of 0.356 mS/cm was obtained.

EXAMPLE 1-6

In the same manner as in Example 1-1, 48.4 g (0.2 mole) of 10-hydroxydecyl methacrylate was reacted with 36.8 g (0.24 mole) of phosphorus oxychloride in the presence of 24.3 g (0.24 mole) of triethylamine using diethyl ether as a solvent (First Dropping Step). Subsequently, Second Dropping Step was further carried out by adding dropwise 12.6 g (0.7 mole) of distilled water and 40.5 g (0.4 mole) of triethylamine to the reaction mixture.

The reaction mixture was added to 0.4 N dilute aqueous hydrochloric acid, and the mixture was stirred, and the ether was further added to allow separation of an organic layer. Using a separatory funnel, the organic layer was further washed thrice with 0.4 N dilute aqueous hydrochloric acid, and subsequently twice with 1% salt solution.

Two-hundred milliliters of ion-exchanged water was added to the organic layer, and the mixture was stirred at room temperature for 12 hours, to convert a trace amount of unreacted P—Cl compound to P—OH (hydrolysis). Five grams of activated charcoal (Wako Pure Chemical) was added to the organic layer to decolorize the organic layer, and thereafter, the ether was distilled off under reduced pressure, to give a desired phosphate monoester (MDP) as an oily product. The purity of the MDP in this oily product as determined by HPLC was 94.0%, and the electric conductivity was 0.245 mS/cm.

Comparative Example 1-4

In the same scale and manner as in Example 1-6, the procedures were carried out up to Second Dropping Step. After the dropwise addition was terminated, a reaction mixture was stirred in this state for additional 2 hours. The hydrochloride of triethylamine was subjected to suction filtration with a filter paper, and the obtained filtrate was washed with water (thrice with 200 ml each of water) by using a separatory funnel. The organic layer was dehydrated and dried with anhydrous sodium sulfate, and the ether was distilled off from the organic layer under reduced pressure, to give a phosphate monoester comprising MDP as a main component. The electric conductivity of the resulting product was 0.632 mS/cm.

The following dental adhesives were prepared using each of these phosphate monoesters. Specifically, there were mixed and dissolved 50 parts by weight of 2,2-bis[methacryloyloxy polyethoxyphenyl]propane (having ethoxy groups in an average number of 2.6 in a molecule, hereinafter referred to as D-2.6E), 10 parts by weight of neopentyl glycol dimethacrylate (hereinafter referred to as NPG), 15 parts by weight of hydroxyethyl methacrylate (HEMA), 25 parts by weight of the phosphate monoester (MDP) prepared in Examples 1-1 to 1-6 and Comparative Examples 1-1 to 1-4, 1.5 parts by weight of benzoyl peroxide (BPO) as a polymerization catalyst, 0.5 parts by weight of camphorquinone, 0.02 parts by weight of dibutylhydroxytoluene (BHT) as a stabilizer, and 0.01 parts by weight of hydroquinone monomethyl ether, to give a dental adhesive. The number of days for gelation for each of these dental adhesives was obtained by the method described above.

In addition, the adhesive strength to dentine for each of the dental adhesives was measured by the method described above. In this test, the adhesion test was carried out after storing the dental adhesive comprising the phosphate monoester at 45° C. for 30 days. The resulting adhesive strength was compared with the adhesive strength immediately after preparation of the adhesive (before storage). The results are also shown in Table 2.

It is clear from Table 2 that there is found a remarkable correlation between the electric conductivity of the MDP contained in the dental adhesive and the number of days for gelation, and the dental adhesives comprising MDP of which electric conductivity is 0.5 mS/cm or less have excellent storage stability. In addition, the lower the electric conductivity, the smaller the degree of lowering the adhesive strength of the dental adhesive after storage.

TABLE 1

| Examples | Amount of Phosphate Oxychloride (mole)* | Amount of Triethylamine | | Purity of MDP (%) | Electric Conductivity (mS/cm) |
|---|---|---|---|---|---|
| | | First Dropping | Second Dropping | | |
| 1-1 | 0.12 | 0.12 | 0.20 | 93.5 | 0.308 |
| 1-2 | 0.12 | 0.12 | 0.22 | 95.0 | 0.389 |
| 1-3 | 0.10 | 0.10 | 0.18 | 93.2 | 0.452 |
| 1-4 | 0.09 | 0.09 | 0.17 | 92.0 | 0.287 |
| Comparative Examples | | | | | |
| 1-1 | 0.12 | 0.12 | 0.24 | 92.4 | 0.524 |
| 1-2 | 0.12 | 0.12 | 0.30 | 94.7 | 0.581 |
| 1-3 | 0.15 | 0.15 | 0.30 | 93.6 | 0.696 |

*Amount added to 0.1 moles of hydroxydecylmethacrylate.

TABLE 2

| Examples | Electric Conductivity (mS/cm) | Number of Days for Gelation | Adhesive Strength to Dentine (MPa) | |
|---|---|---|---|---|
| | | | Initial | After Storage for 30 days at 45° C. |
| 1-6 | 0.245 | 350 days or more | 7.5 | 6.2 |
| 1-4 | 0.287 | 350 days or more | 7.2 | 5.8 |
| 1-1 | 0.308 | 345 | 6.7 | 6.0 |
| 1-5 | 0.356 | 310 | 6.5 | 5.9 |
| 1-2 | 0.389 | 305 | 7.3 | 6.3 |
| 1-3 | 0.452 | 268 | 6.9 | 5.4 |
| Comparative Examples | | | | |
| 1-1 | 0.524 | 156 | 6.3 | 3.2 |
| 1-2 | 0.581 | 125 | 7.1 | 3.7 |
| 1-4 | 0.632 | 70 | 5.7 | 3.0 |
| 1-3 | 0.696 | 70 | 6.0 | 2.6 |

EXAMPLE 2-1

Preparation of MDP (1) Preparation of Monohydroxy(meth)acrylate Compound (10-Methacryloyloxydecan-1-ol) as Raw Material There were reacted 21.8 g (0.25 mole) of methacrylic acid and 52.9 g (0.30 mole) of 1,10-decanediol at 80° C. to prepare an ester. In this reaction, 3.6 g of p-toluenesulfonic acid as a catalyst and 0.2 g of 2,2'-methylenebis(4-ethyl-6-tert-butylphenol) as a polymerization inhibitor were added.

The filtration and the washing with an aqueous alkali solution were carried out to remove an unreacted diol, methacrylic acid, and a catalyst acid. After the solvent was distilled off, 51.5 g of a mixture comprising a methacrylic acid monoester (=10-methacryloyloxydecan-1-ol, which is a raw material for the preparation of the phosphate monoester) and a methacrylic acid diester as a by-product was obtained. The above ester mixture was identified by liquid chromatography, and as a result, the mixture contained 71 mole % monoester and 29 mole % diester.

(2) Preparation of Compound Having —P(O)Cl$_2$ Group (First Dropping Step of Amine)

The amount 51.5 g of the above ester mixture (content of 10-methacryloyloxydecan-1-ol: 0.14 mole) and 17.1 g (0.17 mole) of triethylamine were dissolved in 100 ml of diethyl ether, and the resulting solution was placed in a dropping funnel to be connected to a reaction vessel. The reaction vessel was charged with a solution prepared by dissolving 25.8 g (0.17 mole) of phosphorus oxychloride in 100 ml of diethyl ether, and the internal temperature was cooled to −40° C. With vigorously stirring the phosphorus oxychloride solution, the solution of 10-methacryloyloxydecan-1-ol and triethylamine in the dropping funnel was gradually added dropwise over a period of one hour to the phosphorus oxychloride solution. After the termination of dropwise addition, the reaction mixture was stirred for additional 30 minutes at −20° C.

(3) Preparation of Phosphate Monoester by Hydrolysis of Phosphate Monoester Chloride (Second Dropping Step of Amine)

The reaction mixture obtained in Step (2) was heated to 0° C., and stirred for additional one hour. A mixed solution of 15.3 g (0.85 mole) of distilled water and 28.5 g (0.28 mole; a total amount of amine together with the amount added in First Dropping Step being 0.45 mole, which was 2.65 times by mole to phosphorus oxychloride) of triethylamine was added dropwise to the reaction mixture. The reaction mixture was kept at 0° C., and gradually hydrolyzed over a period of 30 minutes.

(4) Washing Step

The reaction mixture was washed thrice with 100 ml each of 0.4 N hydrochloric acid to extract and remove the precipitated hydrochloride of triethylamine, and additionally washed twice with 100 ml each of 2% salt solution.

(5) Purification Step

Five grams of activated charcoal (manufactured by Wako Pure Chemical) was added to the organic layer after water was extracted therefrom, and the mixture was stirred for one hour to decolorize the mixture. One-hundred milligrams of BHT was added as a polymerization inhibitor to the organic layer from which activated charcoal was removed by filtration with a filter paper, and the solvent was distilled off under reduced pressure, to give about 61.0 g of a highly viscous liquid residue. The above residue was identified by means of liquid chromatography, and as a result, the residue was found to be a mixture of MDP, which is a phosphate monoester of 10-methacryloyldecan-1-ol, and a methacrylic acid diester of 1,10-decanediol.

The methacrylic acid diester contained in the residue was extracted with 180 ml of n-hexane. The resulting residue was dried under reduced pressure to remove moisture, to give 43.6 g of a liquid compound. The liquid chromatography assay was performed, and as a result, it was confirmed that the compound was MDP of which purity was 97.5%. The electric conductivity of the resulting MDP was measured and found to be 0.412 mS/cm.

EXAMPLE 2-2

The above procedures were carried out up to the washing step (4) in the same scale as in Example 2-1. Thereafter, 200 ml of distilled water was added to an organic layer, and the mixture was stirred at room temperature for 12 hours (hydrolysis of remaining phosphate monoester chloride). Subsequently, the above procedures of the purification step (5) or thereafter in Example 2-1 was carried out to prepare MDP. The electric conductivity of the MDP was 0.245 mS/cm.

EXAMPLE 2-3

Comparative Examples 2-1 and 2-2

The same procedures as in Example 2-2 were carried out except for using triethylamine in an amount shown in Table 3 as an entire dropping amount of triethylamine to phosphorus oxychloride, to prepare MDP. The electric conductivity for each of the resulting MDPs is summarized in Table 3.

Further, the following dental adhesives were prepared using each of these MDPs. Specifically, there were mixed and dissolved 50 parts by weight of D-2.6E, 30 parts by weight of NPG, 20 parts by weight of the prepared MDP, 1 part by weight of BPO as a polymerization catalyst, 0.05 parts by weight of BHT as a stabilizer, and 0.1 parts by weight of hydroquinone monomethyl ether, to give a dental adhesive. The number of days for gelation for each of these dental adhesives was obtained by the method described above. The results are shown in Table 3.

In addition, the adhesive strength to dentine of the adhesive was evaluated by the method described above. In this test, the adhesion test was carried out after storing the dental adhesive comprising the phosphate monoester at 50° C. for 30 days. The resulting adhesive strength was compared with the adhesive strength immediately after preparation of the adhesive (before storage). The results are shown in Table 3.

TABLE 3

| Example | Entire Dropping Amount of Amine (mole) | Electric Conductivity of MDP (mS/cm) | Number of days for Gelation | Adhesive Strength to Enamel (MPa) | |
|---|---|---|---|---|---|
| | | | | Initial | After Storage for 30 days at 50° C. |
| 2-1 | 2.65 | 0.432 | 273 days | 7.2 | 5.5 |
| 2-2 | 2.65 | 0.287 | 350 days or more | 7.2 | 6.0 |
| 2-3 | 2.83 | 0.392 | 310 days | 7.3 | 5.8 |
| Comp. Ex. 2-1 | 3.23 | 0.581 | 98 days | 7.0 | 3.2 |
| 2-2 | 3.50 | 0.620 | 72 days | 5.7 | 3.0 |

It is clear from Table 3 that there are remarkable correlations among each of the electric conductivity of the MDP, the number of days for gelation for the dental adhesive comprising the MDP, and further the adhesive strength to dentine (particularly after storing at 50° C. for 30 days), and the entire dropping amount of amine, and that those MDPs having an electric conductivity of 0.5 mS/cm or less, particularly 0.3 mS/cm or less as in Example 2-2, have excellent storage stability.

EXAMPLE 3-1

Preparation of MDP (1) Preparation of (Meth)acrylic Acid Monoester (10-Methacryloyloxydecan-1-ol)

A three-neck flask was charged with 71.7 g (0.83 mole) of methacrylic acid and 174.0 g (1.00 mole, 1.2 times by mole to methacrylic acid) of 1,10-decanediol having a carbonyl value of 0.03 mole %, and 12 g of p-toluenesulfonic acid as a catalyst and 0.5 g of 2,2'-methylenebis(4-ethyl-6-tert-butylphenol) as a polymerization inhibitor were added thereto. The resulting mixture was heated to 80° C. to give a uniform solution, and the mixture in the flask was sequentially monitored by liquid chromatography (column: Unisil QC18, manufactured by G.L. Science).

The pressure inside the flask was gradually reduced, and with blowing oxygen into the flask and stirring the mixture, the esterification reaction was carried out at 80° C. and the formed water was removed by distillation. When 50% of methacrylic acid was used for the reaction, the internal pressure was reduced to 6.7 kPa. When 62% of methacrylic acid was used for the reaction, the reaction mixture was neutralized with 750 ml of a 10% aqueous sodium hydrogencarbonate solution to stop the reaction. The reaction mixture was cooled to room temperature, and diluted by adding 200 ml of n-hexane. A precipitated unreacted diol in an amount of 100.4 g (0.58 mole) at this time was separated by filtration, and recovered. The filtrate was washed with a 2% aqueous sodium carbonate solution. One-hundred milligrams of activated charcoal and 14 g of anhydrous sodium sulfate were added to the organic layer after removal of the aqueous layer, and the mixture was allowed to stand at room temperature for 12 hours, and then filtered.

Fifty milligrams of MEHQ was added to the recovered filtrate, and n-hexane was distilled off at 30° C. or less under reduced pressure, to give 108.7 g of a mixture of a methacrylic acid monoester and a methacrylic acid diester of the diol. The ester mixture was identified by means or liquid chromatography, and as a result, the mixture contained 78 mole % monoester and 22 mole % diester (monoester/diester=3.5), and an unreacted diol is only contained in a trace amount.

(2) Preparation of Compound Having —P(O)Cl$_2$ Group (First Dropping Step of Amine)

The amount 108.7 g of the ester mixture (content of 10-methacryloyloxydecan-1-ol: 0.33 mole) and 39.9 g (0.40 mole) of triethylamine were dissolved in 120 ml of diethyl ether, and the resulting solution was placed in a dropping funnel, and the dropping funnel was connected to a reaction vessel. The reaction vessel was charged with a solution prepared by dissolving 60.4 g (0.40 mole) of phosphorus oxychloride in 120 ml of diethyl ether, and the internal temperature was cooled to −40° C. With vigorously stirring the phosphorus oxychloride solution, the solution of the ester mixture and triethylamine in the dropping funnel was gradually added dropwise over a period of one hour to the phosphorus oxychloride solution. After the termination of dropwise addition, the reaction mixture was stirred at −20° C. for additional 30 minutes.

(3) Preparation of Phosphate Monoester by Hydrolysis of Phosphate Monoester Chloride (Second Dropping Step of Amine)

The reaction mixture obtained in Step (2) was heated to 0° C., and stirred for additional one hour. A mixed solution of 30 g (1.67 mole) of distilled water and 65.8 g (0.65 mole; a total amount of amine together with the amount added in First Dropping Step being 1.06 mole, which was 2.65 times by mole to phosphorus oxychloride) of triethylamine was added dropwise to the reaction mixture. The reaction mixture was kept at 0° C., and gradually hydrolyzed over a period of 30 minutes.

(4) Step for Removal of Amine Salt by Extraction

The reaction mixture was washed thrice with 100 ml each of 0.4 N hydrochloric acid to extract and remove the precipitated hydrochloride of triethylamine, and additionally washed twice with 100 ml each of 2% salt solution. Thereafter, 200 ml of distilled water was added to the organic layer, and the mixture was stirred at room temperature for 12 hours (hydrolysis of remaining phosphate monoester chloride).

(5) Purification Step

One-hundred milligrams of activated charcoal was added to the organic layer after extraction of water, and the mixture was allowed to stand for 12 hours at room temperature. One-hundred milligrams of BHT was added as a polymerization inhibitor to the organic layer obtained after activated charcoal was removed by filtration, and the solvent was distilled off under reduced pressure, to give about 131.1 g of a highly viscous liquid residue. The residue was identified by means of liquid chromatography, and as a result, the residue was found to be a mixture of a phosphate monoester (MDP) and a methacrylic acid diester of 1,10-decanediol. In addition, the molar ratio of MDP/methacrylic acid diester was 3.5, which was the same as the molar ratio of methacrylic acid monoester/methacrylic acid diester mentioned above, so that it was found that all of the methacrylic acid monoesters were converted to the MDP by phosphate esterification.

The methacrylic acid diester contained in the residue was extracted with 400 ml of n-hexane. The extract was dried under reduced pressure to remove moisture, to give 102.0 g of a liquid compound. The liquid chromatography assay was performed, and as a result, it was confirmed that the compound was found to be MDP having purity of 97.5%.

In addition, the total amount of the methacrylic acid diester of the diol, obtained as a by-product, was 29.1 g (0.09 mole).

The electric conductivity of the resulting MDP was measured, and as a result, the electric conductivity was found to be 0.287 mS/cm. Also, the light transmittance of the MDP was 97.5%.

EXAMPLE 3-2

The same procedures as in Example 3-1 were carried out except for using 1,10-decanediol having a carbonyl value of 0.07 mole %, and changing the reaction ratio of methacrylic acid to 85% and the entire dropping amount of triethylamine to phosphorus oxychloride to 2.83 times by mole to prepare MDP.

Comparative Example 3-1

The same procedures as in Example 3-1 were carried out except for using 1,10-decanediol having a carbonyl value of 0.14 mole %, and changing the reaction ratio of methacrylic acid to 98% and the entire dropping amount of triethylamine to phosphorus oxychloride to 3.23 times by mole to prepare MDP.

Each of the dental adhesives using the MDPs prepared in Examples 3-1, 3-2 and Comparative Example 3-1 was evaluated for the number of days for gelation, the adhesive strength to dentine, and the color tone suitability as mentioned above. The results are shown in Table 5.

Incidentally, in the evaluation for the number of days for gelation and the adhesive strength to dentine, the following dental adhesive was prepared and used. Specifically, there were mixed and dissolved 50 parts by weight of D-2.6E, 30 parts by weight of NPG, 20 parts by weight of the phosphate monoester (MDP), 1 part by weight of BPO, 0.05 parts by weight of BHT, and 0.1 parts by weight of hydroquinone monomethyl ether, to give a dental adhesive. In addition, in the evaluation of the color tone suitability, the dental adhesive as prepared in Table 4 was used. Hereinafter, the dental adhesives used in the evaluation for these items were also prepared in the same manner as above.

TABLE 4

| Components | Parts by Weight |
|---|---|
| MDP | 30 |
| 2-Hydroxyethyl methacrylate | 35 |
| Bis-GMA | 30 |
| dl-Camphorquinone | 1 |
| Ethyl Dimethylaminobenzoate | 2 |

TABLE 5

| Item | Example 3-1 | Example 3-2 | Comp. Ex. 3-1 |
|---|---|---|---|
| Carbonyl Value of Diol (mole %/mole of Diol) | 0.03 | 0.07 | 0.14 |
| Molar Ratio of Diol/Methacrylic Acid | 1.2 | 1.2 | 1.2 |
| Reaction Ratio of Methacrylic Acid (%) | 62 | 85 | 98 |
| Entire Dropping Amount of Amine (mole/mole of Phosphate Oxychloride) | 3.5 | 2.4 | 1.8 |
| Molar Ratio of Monoester/Diester (MDP/Diester) | 3.5 | 2.4 | 1.8 |
| Yield of MDP (mole %/mole of Reacted Diol) | 77.8 | 70.6 | 64.3 |
| Purity of MDP (%) | 97.5 | 96.7 | 93.3 |
| Amount of By-Product Diester (g/mole of Diol) | 29.1 | 49.9 | 66.6 |
| Amount of Unreacted Diol (g/mole of Diol) | 100.4 | 78.8 | 69.3 |
| Electric Conductivity of MDP (mS/cm) | 0.287 | 0.392 | 0.581 |
| Number of Days for Gelation | 350 days or more | 310 days | 98 days |
| Adhesive strength to Dentine (MPa) | | | |
| Initial | 7.2 | 7.3 | 7.0 |
| After Storage for 30 days at 50° C. | 6.0 | 5.8 | 3.2 |
| Light Transmittance of MDP (%) | 97.5 | 92.2 | 95.7 |
| Color Tone Suitability | Excel. | Excel. | Poor |

It is clear from Table 5 that the conventional problems as recognized in Comparative Example 3-1, namely I) low yield of the phosphate monoester, II) coloration, and III) poor storage stability, are solved in Examples 3-1 and 3-2.

EXAMPLE 3-3

Comparative Examples 3-2 and 3-3

The same procedures as in Example 3-1 were carried out except for reacting methacrylic acid at reaction ratios shown in Table 6, to prepare MDP. The molar ratio of MDP/diester, the yield of the MDP, the purity of the MDP, the amount of a by-product diester, and the amount of an unreacted diol are summarized in Table 6.

Comparative Example 3-4

The same procedures as in Example 3-1 were carried out except for reacting the diol in the amount of 0.6 times by mole to methacrylic acid and changing the reaction ratio of methacrylic acid to 83%, to prepare MDP. The molar ratio of MDP/diester, the yield of the MDP, the purity of the MDP, the amount of a by-product diester, and the amount of an unreacted diol are summarized in Table 6.

EXAMPLE 3-4

The same procedures for methacrylic acid esterification as in Example 3-1 were carried out except for reacting the diol at 2.5 times by mole to methacrylic acid and changing the reaction ratio of methacrylic acid to 89%, to give a mixture of a monoester and a diester. Methacrylic acid was added to an unreacted diol in such an amount that the ratio of the diol to methacrylic acid is the same as the first esterification, namely 2.5 times by mole, and the reaction was carried out at a reaction ratio of methacrylic acid of 89%.

Each mixture of the monoester and the diester obtained in the two methacrylic acid esterification reactions was combined, and MDP was prepared therefrom under the same procedures as in Example 3-1. The molar ratio of MDP/diester, the yield of the MDP, the purity of the MDP, the amount of the by-product diester, and the amount of the unreacted diol are summarized in Table 6.

TABLE 6

| | Comp. Ex. 3-2 | Example 3-1 | Example 3-3 | Comp. Ex. 3-3 | Comp. Ex. 3-4 | Example 3-4 |
|---|---|---|---|---|---|---|
| Molar Ratio of Diol/Methacrylic Acid | 1.2 | 1.2 | 1.2 | 1.2 | 0.6 | 2.5 |
| Reaction Ratio of Methacrylic Acid (%) | 30 | 62 | 85 | 98 | 83 | 89 |
| Molar Ratio of Monoester/Diester (= MDP/Diester) | 3.8 | 3.5 | 2.4 | 1.8 | 1.6 | 4.3 |
| Yield of MDP | 50.8 | 102.0 | 119.8 | 119.9 | 190.6 | 128.1 |

TABLE 6-continued

|  | Comp. Ex. 3-2 | Example 3-1 | Example 3-3 | Comp. Ex. 3-3 | Comp. Ex. 3-4 | Example 3-4 |
|---|---|---|---|---|---|---|
| (g/mole of Diol) |  |  |  |  |  |  |
| Purity of MDP (%) | 98.2 | 97.5 | 96.7 | 93.3 | 92.4 | 98.5 |
| Amount of By-Product Diester (g/mol of Diol) | 13.4 | 29.1 | 49.9 | 66.6 | 119.1 | 29.8 |
| Amount of Unreacted Diol (g/mol of Diol) | 138.0 | 100.4 | 78.8 | 69.3 | 0.2 | 85.4 |

In Examples 3-1 and 3-3 and Comparative Examples 3-2 and 3-3 have the same initial amount of diol/methacrylic acid, with changing the reaction ratio of methacrylic acid. In Comparative Example 3-2 where the reaction ratio is low, the yield of the MDP is too small even though the purity is high; on the other hand, in Comparative Example 3-3 where the reaction ratio is high, only an unnecessary diester increases without increasing the yield of the MDP as compared with Example 3-3. Therefore, these comparative examples are undesirable. Therefore, as in Examples 3-1 and 3-3, it is desirable to improve the yield of MDP by controlling to the reaction ratio of methacrylic acid of from 60 to 90%, and thereby reducing the amount of a by-product diester.

In addition, in Comparative Example 3-4 where the initial amount of the diol to methacrylic acid is small, almost all of the diols are reacted, but the diol used in the formation of diester also increases, thereby making it undesirable. On the other hand, in Example 3-4 (where methacrylic acid esterification was carried out twice) where the initial amount of the diol to methacrylic acid is large, the yield of the MDP increases while the amount of a by-product diester decreases, thereby giving desirable results.

Further, the smaller the amount of a by-product diester (the ratio of MDP/diester is large), the higher the purity of the MDP can be obtained due to ease in extraction procedures.

From the above, high-purity phosphate monoester (MDP) can be obtained at a high yield by supplying an equal amount or slightly excessive amount of diol to methacrylic acid as an initial amount of the diol, and controlling to the reaction ratio of methacrylic acid of from 60 to 90%.

EXAMPLE 3-5

Comparative Example 3-5

The same procedures as in Example 3-1 were carried out except for using a diol having a different carbonyl value from that of Example 3-1 as shown in Table 7, to prepare MDP. The light transmittance of the MDP and the color tone suitability of the dental adhesive prepared by using the MDP in the manner described above were evaluated. The results are summarized in Table 7.

EXAMPLE 3-6

The purification with activated charcoal was carried out for the MDP of Comparative Example 3-5 of which light transmittance was low. Specifically, the MDP of Comparative Example 3-5 was dissolved in ethanol at about 10% by weight, and the activated charcoal powder was dispersed at 5% by weight in the ethanol solution, and the mixture was stirred. Thereafter, the activated charcoal powder was separated by filtration by means of suction filtration, and ethanol in the filtrate was distilled off by a rotary evaporator, to give an oily MDP. The light transmittance of the MDP, and the color tone suitability of the dental adhesive prepared by using the MDP as described above were evaluated. The results are shown in Table 7.

EXAMPLE 3-7

The purification by column chromatography was carried out for the MDP of Comparative Example 3-5 of which light transmittance was low. Specifically, the MDP of Comparative Example 3-5 was treated by column chromatography using Wako gel 40$C_{18}$ (manufactured by Wako Pure Chemical Industries, Ltd.) as a carrier for reverse-phase chromatography and water/methanol=3/7 as an eluent. The solvents were distilled off by a rotary evaporator, to give an oily MDP. The light transmittance of the MDP, and the color tone suitability of the dental adhesive prepared by using the MDP as described above were evaluated. The results are shown in Table 7.

TABLE 7

|  | Example 3-1 | Example 3-5 | Example 3-6 | Example 3-7 | Comp. Ex. 3-5 |
|---|---|---|---|---|---|
| Carbonyl Value of Diol (mol %/mole of Diol) | 0.03 | 0.07 | 9.14 | 0.14 | 0.14 |
| Light Transmittance (%) of MDP | 97.5 | 92.2 | 95.7 | 93.3 | 87.9 |
| Color Tone Suitability | Excel. | Excel. | Excel. | Excel. | Poor |

In Comparative Example 3-5 where the carbonyl value of the diol is 0.1 or more, the light transmittance of the MDP is 90% or less, and further, the dental adhesive prepared therefrom is not satisfactory in terms of the color tone suitability. On the other hand, in Examples 3-1 and 3-5 where the MDP is prepared from the diol having a low carbonyl value, the dental adhesives prepared therefrom have excellent color tone suitability.

Moreover, even in a case of Comparative Example 3-5 where the MDP has a low light transmittance, it is found that purifying by such means as activated charcoal (Example 3-6), column chromatography (Example 3-7), or the like increases the light transmittance of MDP and thus the dental adhesive prepared therefrom having excellent color tone suitability can be obtained. However, in consideration of the simplification of the steps and the reduction of costs entailed for purification, it is preferable to prepare MDP by using a diol having a low carbonyl value in order to obtain an MDP composition without coloration.

EXAMPLE 3-8

The same procedures as in Example 3-1 were carried out up to the washing step in item (4), and thereafter the purification step in item (5) or thereafter were carried out while omitting hydrolysis of the remaining phosphate monoester chloride, to prepare MDP. The electric conductivity of the MDP, the number of days for gelation of the dental adhesive prepared from the MDP, and the adhesive strengths to dentine immediately after preparation of the adhesive (before storage) and after storage at 50° C. for 30 days are summarized in Table 8.

EXAMPLE 3-9

Comparative Examples 3-6 and 3-7

The same procedures as in Example 3-1 were carried out except for using triethylamine in an amount shown in Table 8 as an entire dropping amount of triethylamine to phosphorus oxychloride, to prepare MDP. The electric conductivity of the MDP, the number of days for gelation of the dental adhesive prepared from the MDP, and the adhesive strengths to dentine immediately after preparation of the dental adhesive (before storage) and after storage at 50° C. for 30 days are summarized in Table 8.

TABLE 8

| Example | Entire Dropping Amount of Amine (mole) | Electric Conductivity of MDP (mS/cm) | Number of Days for Gelation | Adhesive Strength to Enamel (MPa) | |
|---|---|---|---|---|---|
| | | | | Initial | After Storage for 30 days at 50° C. |
| 3-8 | 2.65 | 0.432 | 273 days | 7.2 | 5.5 |
| 3-1 | 2.65 | 0.287 | 350 days or more | 7.2 | 6.0 |
| 3-9 | 2.83 | 0.392 | 310 days | 7.3 | 5.8 |
| Comp. Ex. 3-6 | 3.23 | 0.581 | 98 days | 7.0 | 3.2 |
| 3-7 | 3.50 | 0.620 | 72 days | 5.7 | 3.0 |

It is clear from Table 8 that there is found a remarkable correlation among each of the electric conductivity of MDP, the number of days for gelation of the dental adhesive prepared from MDP, and the adhesive strength to dentine (particularly after storage at 50° C. for 30 days), and the entire dropping amount of amine, and it is found that the storage stability of MDP having an electric conductivity of 0.5 mS/cm or less, particularly 0.3 mS/cm or less as in Example 3-1, is excellent. In addition, when Example 3-1 is compared with Example 3-8, both examples having the same dropping amount of amine, it is found that MDP having further excellent storage stability is obtained in Example 3-1 where the remaining phosphate monoester chloride is hydrolyzed.

EXAMPLE 4-1

Preparation of 6-Methacryloyloxyhexyl dihydrogenphosphate (Compound 1a of Table 9)

(1) Preparation of (Meth)acrylic Acid Monoester (6-Methacryloyloxyhexan-1-ol)

A three-neck flask was charged with 71.7 g (0.83 mole) of methacrylic acid and 118.18 g (1.00 mole, 1.2 times by mole to methacrylic acid) of 1,6-hexanediol (Compound 6a of Table 10) having a carbonyl value of 0.03 mole %-, and 12 g of p-toluenesulfonic acid as a catalyst and 0.5 g of 2,2'-methylenebis(4-ethyl-6-tert-butylphenol) as a polymerization inhibitor were added thereto. The resulting mixture was heated to 80° C. to give a uniform solution, and the mixture in the flask was sequentially monitored by liquid chromatography (column: Unisil QC18, manufactured by G.L. Science).

The pressure inside the flask was gradually reduced, and with blowing oxygen into the flask and stirring the mixture, the esterification reaction was carried out at 80° C., and the formed water was removed by distillation. When 65% of methacrylic acid was used for the reaction, the reaction mixture was neutralized with 750 ml of a 10% aqueous sodium hydrogencarbonate solution to stop the reaction. The reaction mixture was cooled to room temperature, and diluted by adding 200 ml of n-hexane. A precipitated unreacted diol in an amount of 66.2 g (0.56 mole) at this time was separated by filtration, and recovered. The filtrate was washed with a 2% aqueous sodium carbonate solution. One-hundred milligrams of activated charcoal and 14 g of anhydrous sodium sulfate were added to the organic layer after removal of the aqueous layer, and the mixture was allowed to stand at room temperature for 12 hours, and then filtered.

From the recovered filtrate n-hexane was distilled off at 30° C. or less under reduced pressure, to give a mixture of a methacrylic acid monoester and a methacrylic acid diester of the diol.

(2) Preparation of Compound Having —P(O)Cl$_2$ Group (First Dropping Step of Amine)

The amount 85.0 g of the ester mixture (content of 6-methacryloyloxyhexan-1-ol: 0.32 mole) and 39.9 g (0.40 mole) of triethylamine were dissolved in 120 ml of diethyl ether, and the resulting solution was placed in a dropping funnel, and the dropping funnel was connected to a reaction vessel. The reaction vessel was charged with a solution prepared by dissolving 60.4 g (0.40 mole) of phosphorus oxychloride in 120 ml of diethyl ether, and the internal temperature was cooled to −40° C. With vigorously stirring the phosphorus oxychloride solution, the solution of the ester mixture and triethylamine in the dropping funnel was gradually added dropwise over a period of one hour to the phosphorus oxychloride solution. After the termination of dropwise addition, the reaction mixture was stirred at −20° C. for additional 30 minutes.

(3) Preparation of Phosphate Monoester by Hydrolysis of Phosphate Monoester Chloride (Second Dropping Step of Amine)

The reaction mixture obtained in Step (2) was heated to 0° C., and stirred for additional one hour. A mixed solution of 30 g (1.67 mole) of distilled water and 65.8 g (0.65 mole; a total amount of amine together with the amount added in First Dropping Step being 1.06 mole, which was 2.65 times by mole to phosphorus oxychloride) of triethylamine was added dropwise to the reaction mixture. The reaction mixture was kept at 0° C., and gradually hydrolyzed over a period of 30 minutes.

(4) Step for Removal of Amine Salt by Extraction

The reaction mixture was washed thrice with 100 ml each of 0.4 N hydrochloric acid to extract and remove a precipitated hydrochloride of triethylamine, and additionally washed twice with 100 ml each of 2% salt solution. Thereafter, 200 ml of distilled water was added to the organic layer, and the mixture was stirred at room temperature for 12 hours (hydrolysis of remaining phosphate monoester chloride).

(5) Purification Step

One-hundred milligrams of activated charcoal was added to the organic layer after extraction of water, and the mixture was allowed to stand for 12 hours at room temperature. One-hundred milligrams of BHT was added as a polymerization inhibitor to the organic layer obtained after activated charcoal was removed by filtration, and the solvent was distilled off under reduced pressure, to give about 112 g of a highly viscous liquid residue. The residue was identified by means of liquid chromatography, and as a result, the residue was found to be a mixture of a phosphate monoester (6-methacryloyloxyhexyl dihydrogenphosphate) and a methacrylic acid diester of 1,6-hexanediol. In addition, the molar ratio of phosphate monoester/methacrylic acid diester was 3.2.

The methacrylic acid diester contained in the residue was extracted with 400 ml of n-hexane. The extract was dried under reduced pressure to remove moisture, to give 84.8 g of a liquid compound. The liquid chromatography assay was performed, and as a result, it was confirmed that the compound was found to be 6-methacryloyloxyhexyl dihydrogenphosphate (Compound 1a of Table 9) having purity of 98.1%.

The electric conductivity of the resulting phosphate monoester was found to be 0.361 mS/cm, and the light transmittance was 98.1%. In addition, a dental adhesive having the same composition as in Example 1-1 using this phosphate monoester was prepared, and the number of days for gelation was evaluated. As a result, the number of days was found to be 350 days or more (Table 11).

EXAMPLES 4-2 to 4-6

The same procedures as in Example 4-1 were carried out except for using as raw material diols each of Compounds 6b, 6c, 6d, 7a and 7b of Table 10, to prepare each of phosphate monoesters (Compounds 1b, 1c, 1d, 2a and 2b of Table 9). The relationships between the diols and their carbonyl values and between the diols and the desired phosphate monoesters are summarized in Table 11. Here, the molar ratio of the raw material diol to methacrylic acid, the molar ratio of methacrylic acid monoester to triethylamine, and the molar ratio of triethylamine to phosphorus oxychloride were all adjusted to be the same as those in Example 4-1. The light transmittance and the electric conductivity of each of the resulting phosphate monoesters, and the number of days for gelation of the dental adhesive were evaluated in the same manner as in Example 4-1. The results are summarized in Table 11.

EXAMPLE 4-7

Preparation of 4-Methacryloyloxybutyl Dihydrogenphosphate (Compound 1e of Table 9)

The same procedures as in Example 4-1 were carried out except for using 4-methacryloyloxybutan-1-ol (47.4 g, 0.30 mole) as a starting material (ester compound) for First Dropping Step of Amine of item (2) of Example 4-1, and the reactions were carried out with the same molar ratios and procedures on and after item (2) of Example 4-1, to give 4-methacryloyloxybutyl dihydrogenphosphate (Compound 1e). The light transmittance and the electric conductivity of the resulting phosphate monomer, and the number of days for gelation of the dental adhesive were evaluated in the same manner as in Example 4-1. The results are summarized in Table 11.

EXAMPLE 5-1

Preparation of 2-Methacryloyloxyethyl Phenyl Acid Phosphate (Compound 3a of Table 9)

The amount 54.9 g (0.42 mole) of 2-hydroxyethyl methacrylate and 44.8 g (0.44 mole) of triethylamine used as a hydrochloric acid-removing agent were dissolved in diethyl ether, and the resulting solution was placed in a dropping funnel connected to a reaction vessel. The reaction vessel was charged with a diethyl ether solution of 93.3 g of phenyl dichlorophosphate, 1.05 times by mole to 2-hydroxyethyl methacrylate, and the ingredients were cooled to −20° C. and vigorously stirred, and the mixture inside the dropping funnel was gradually added dropwise. Further, an aqueous solution of 55.6 g (0.55 moles) of trimethylamine was added dropwise to the reaction mixture, and the reaction was terminated. The used triethylamine was 2.25 times by mole to phenyl dichlorophosphate. Diethyl ether was added to the reaction mixture, and the precipitated hydrochloride of triethylamine was separated by filtration. The organic layer was washed twice with ion-exchanged water. Dibutylhydroxytoluene was added to the filtrate for extraction. The toluene was distilled off under reduced pressure, to give 96.5 g of a desired product 2-methacryloyloxyethyl phenyl acid phosphate (Compound 3a).

The light transmittance and the electric conductivity of the resulting phosphate monomer were determined. In addition, the same dental adhesive as in Example 1-1 using this phosphate monomer was prepared, and the number of days for gelation and the adhesive strength of the dental adhesive to dentine were evaluated. Further, the same dental adhesive as in Example 3-1 using this phosphate monomer was prepared, and the color tone suitability of the dental adhesive was evaluated. The results are shown in Table 12.

EXAMPLE 5-2

Preparation of 2-Methacryloyloxyethyl Phenyl Acid Phosphate (Compound 3a of Table 9)

The same procedures as in Example 5-1 were carried out up to the filtration step of the hydrochloride of triethylamine. Dibutylhydroxytoluene was added to the filtrate, and thereafter the solvent was removed by a rotary evaporator. The concentrated filtrate was added to distilled water, and an entire amount 66.5 g (0.34 mole) of barium carbonate was added little by little with stirring, and the mixture was stirred for 15 minutes. Subsequently, the mixture was stirred at room temperature for 15 minutes to form barium phosphate. The unreacted barium carbonate was filtered, and the filtrate was washed thrice with toluene. 6 N Hydrochloric acid was added thereto, and thereafter, the mixture was subjected to extraction with toluene. Activated charcoal was added to the separated organic layer, and the mixture was allowed to stand for 12 hours, and thereafter the activated charcoal was separated by filtration. The organic layer was washed four times with ion-exchanged water, and thereafter, the toluene was distilled off, to give a desired product 2-methacryloyloxyethyl phenyl acid phosphate (Compound 3a).

The light transmittance and the electric conductivity of the resulting phosphate monomer, and the number of days for gelation, the adhesive strength to dentine and the color tone suitability of the dental adhesive were evaluated in the same manner as in Example 5-1. The results are shown in Table 12.

EXAMPLE 6

Preparation of 2-Methacryloyloxyethyl Phenyl Phosphonic Acid (Compound 3b of Table 9)

The same procedures as in Example 5-2 were carried out with the same raw material molar ratios as in Example 5-2, except that in item (1) of Example 5-2, dichlorophosphonic acid was used in place of the used raw material phenyl dichlorophosphate, to give a desired product 2-methacryloyloxyethyl phenyl phosphonic acid (Compound 3b).

The light transmittance and the electric conductivity of the resulting phosphate monomer, and the number of days for gelation, the adhesive strength to dentine and the color tone suitability of the dental adhesive were evaluated in the same manner as in Example 5-1. The results are shown in Table 12.

EXAMPLE 7

Preparation of Mixture of 10-Methacryloyloxydecyl Dihydrogenphosphate and bis(1O-Methacryloyloxydecyl) Hydrogenphosphate (Compound 4 of Table 9)

The same procedures as in Example 3-1 were carried out, except that in item (2) of Example 3-1, phosphorus oxychloride was reacted in an amount 0.8 times by mole to the methacrylic acid monoester in the mixture, and molar ratios of other raw materials were the same as in Example 3-1, to give a mixture of phosphate monoester and phosphate diester. The mixture of the resulting phosphate monoester and phosphate diester was analyzed by HPLC, and as a result the molar ratio of the phosphate monoester to the phosphate diester was 58/42. The light transmittance and the electric conductivity of the resulting phosphate monomer, and the number of days for gelation, the adhesive strength to dentine and the color tone suitability of the dental adhesive were evaluated in the same manner as in Example 5-1. The results are shown in Table 12.

EXAMPLE 8-1

Preparation of 5-Methacryloyloxypentyl-3-phosphonopropionate (Compound 5a of Table 9)

(1) Preparation of 5-Hydroxypentyl Methacrylate

The same procedures as in item (1) of Example 4-1 were carried out with the same raw material molar ratios except for using 1,5-pentanediol as a raw material, and the resulting monoester and diester were purified by column chromatography, to give a monoester 5-hydroxypentyl methacrylate.

(2) Preparation of Ethyl 3-Diethyl Phosphonopropionate

Equimolar amounts of triethyl phosphite and β-propiolactone were mixed, and the mixture was refluxed at 160° C. for 18 hours to react the components. The reaction mixture was subjected to distillation under reduced pressure, and a distillation fraction at 130° to 135° C. (267 to 533 Pa) was collected, to give ethyl 3-diethyl phosphonopropionate.

(3) Preparation of 2-Carboxyethyl Phosphonate

One-hundred grams (0.42 mole) of ethyl 3-diethyl phosphonopropionate obtained in item (2) above, 300 g of 48% hydrobromic acid and 200 g of formic acid were mixed, and the formed ethyl bromide was distilled off with hydrolyzing at 90° C. After no more ethyl bromide was formed, the reaction mixture was concentrated with heating, and ice-cooled, to allow precipitation of crystals of the product. The crystals were subjected to suction filtration, and washed with a small amount of acetone. Thereafter, the washed crystals were dried in vacuo, to give 2-carboxyethyl phosphonate.

(4) Preparation of 5-Methacryloyloxypentyl-3-Phosphonopropionate (Compound 5a of Table 9)

A reaction vessel was charged with 68.8 g (0.40 mole) of 5-hydroxypentyl methacrylate obtained in item (1), 96.3 g (0.35 moles) of 2-carboxyethyl phosphonate obtained in item (3), 3.5 g of p-toluenesulfonic acid, 3.5 g of dibutylhydroxytoluene and 80 g of toluene, and the ingredients were reacted under reduced pressure of about 40 kPa at about 80° C. with stirring. After reacting for 6 hours, the reaction mixture was cooled to room temperature, and transferred to a separatory funnel. Ethyl acetate was added to the mixture in the separatory funnel, and the mixture was washed twice with water. Anhydrous sodium sulfate was added to the separated organic layer to allow dehydration, and the solvents were distilled off under reduced pressure to give an oily product. An aqueous sodium carbonate solution was added to the oily product, and a desired product was extracted to the aqueous layer. 6 N Hydrochloric acid was added to the aqueous layer to make the mixture acidic, and the mixture was extracted thrice with diethyl ether. Activated charcoal was added to the ether layer, and the mixture was allowed to stand for 12 hours. The activated charcoal was then separated by filtration, and the mixture was washed four times with ion-exchanged water. Thereafter, the ether was distilled off under reduced pressure, to give 48 g of a desired product 5-methacryloyloxypentyl-3-phosphonopropionate (Compound 5a).

The light transmittance and the electric conductivity of the resulting phosphate monomer, and the number of days for gelation, the adhesive strength to dentine and the color tone suitability of the dental adhesive were evaluated in the same manner as in Example 5-1. The results are shown in Table 12.

EXAMPLE 8-2

Preparation of 1°-Methacryloyloxydecyl-3-phosphonopropionate (Compound 5b of Table 9)

(1) Preparation of 10-Hydroxydecyl Methacrylate

The same procedures as in item (1) of Example 5-1 were carried out, and the resulting monoester and diester were purified by column chromatography, to give 10-hydroxydecyl methacrylate.

(2) Preparation of 10-Methacryloyloxydecyl-3-phosphonopropionate (Compound 5b of Table 9)

The amount 58.3 g (0.24 moles) of 10-hydroxydecyl methacrylate obtained in item (1), 30.7 g (0.20 moles) of 2-carboxyethylphosphonic acid, 3.5 g of p-toluenesulfonic acid and 0.35 g of dibutylhydroxytoluene, and the ingredients were subjected to esterification reaction at about 40 kPa and about 100° C. with stirring. Subsequent treatments were carried out in the same manner as in Example 7-1, to give 28 g of a desired product 10-methacryloyloxydecyl-3-phosphonopropionate (Compound 5b).

The light transmittance and the electric conductivity of the resulting phosphate monomer, and the number of days for gelation, the adhesive strength to dentine and the color tone suitability of the dental adhesive were evaluated in the same manner as in Example 5-1. The results are shown in Table 12.

TABLE 10

| Compound | Formula |
|---|---|
| 6a | HO—(CH$_2$)$_6$—OH |
| 6b | HO—(CH$_2$)$_9$—OH |
| 6c | HO—(CH$_2$)$_{12}$—OH |
| 6d | HO—(CH$_2$)$_{16}$—OH |

TABLE 10-continued

| Compound | Formula |
|---|---|
| 7a | HO—(CH$_2$)$_2$—O—⟨benzene ring⟩—O—(CH$_2$)$_2$—OH |
| 7b | HO—(CH$_2$)$_4$—O—⟨benzene ring⟩—O—(CH$_2$)$_4$—OH |

TABLE 11

| Example | Compound | Raw Material Diol | Carbonyl Value of Diol (mole %/mole Diol) | Light Transmittance (%) | Electric Conductivity (mS/cm) | Number of days for Gelation |
|---|---|---|---|---|---|---|
| 4-1 | 1a | 6a | 0.03 | 98.1 | 0.361 | 350 days or more |
| 4-2 | 1b | 6b | 0.04 | 97.8 | 0.392 | 315 days |
| 4-3 | 1c | 6c | 0.05 | 96.5 | 0.372 | 294 days |
| 4-4 | 1d | 6d | 0.04 | 97.1 | 0.358 | 266 days |
| 4-5 | 2a | 7a | 0.03 | 97.6 | 0.292 | 287 days |
| 4-6 | 2b | 7b | 0.04 | 97.3 | 0.321 | 252 days |
| 4-7 | 1e | — | — | 98.7 | 0.325 | 350 days or more |

TABLE 12

| Example | Compound | Light Transmittance (%) | Electric Conductivity (mS/cm) | Number of days for Gelation | Adhesive Strength to Enamel (MPa) Initial | Adhesive Strength to Enamel (MPa) After Storage for 30 days at 45° C. | Color Tone Suitability |
|---|---|---|---|---|---|---|---|
| 5-1 | 3a | 94.5 | 0.402 | 322 days | 7.0 | 6.1 | Excel. |
| 5-2 | 3a | 98.6 | 0.289 | 350 days or more | 7.1 | 6.4 | Excel. |
| 6 | 3b | 97.9 | 0.322 | 350 days or more | 7.3 | 6.5 | Excel. |
| 7 | 4 | 97.2 | 0.361 | 350 days or more | 7.5 | 6.2 | Excel. |
| 8-1 | 5a | 96.5 | 0.387 | 294 days | 6.9 | 5.8 | Excel. |
| 8-2 | 5b | 97.1 | 0.351 | 266 days | 7.1 | 6.2 | Excel. |

INDUSTRIAL APPLICABILITY

According to the present invention, there can be obtained in high purity and at high yield a phosphate compound, which has substantially no problems concerning gelation or solidification owing to the increase in the viscosity during a long-term storage, lowered adhesion strength after storage, and the like, further the phosphate compound having improved color tone. Such a phosphate compound can be used for a dental polymerizable composition comprising the phosphate monomer, the dental polymerizable composition having excellent color tone suitability, excellent storage stability and high adhesive strength.

EQUIVALENT

Those skilled in the art will recognize, or be able to ascertain using simple routine experimentation, many equivalents to the specific embodiments of the invention described in the present specification. Such equivalents are intended to be encompassed in the scope of the following claims.

What is claimed is:

1. An organic phosphate compound having at least one radically polymerizable double bond, at least one phosphate residue having one or two hydroxyl groups, and at least one hydrocarbon group having 4 or more carbon atoms in a molecule, wherein a 10% by weight methanol solution of the organic phosphate compound has an electric conductivity at 25° C. of 0.5 mS/cm or less, and/or the organic phosphate compound has a light transmittance at 455 nm of 90% or more.

2. The organic phosphate compound according to claim 1, wherein the organic phosphate compound has a structure such that a phosphate residue is bound with a hydrocarbon group having 4 or more carbon atoms, an organic group having a (meth)acrylate group, and one hydroxyl group.

3. The organic phosphate compound according to claim 1, wherein the organic phosphate compound has a structure such that a phosphate residue having one or two hydroxyl groups is bound with a (meth)acrylate group via a connecting group having at least one hydrocarbon group having 4 or more carbon atoms.

4. The organic phosphate compound according to claim 3, wherein the connecting group is an aliphatic group having 4 or more carbon atoms.

5. The organic phosphate compound according to claim 3, wherein the organic phosphate compound has a structure such that a phosphate residue having two hydroxyl groups is bound with a (meth)acrylate group via a connecting group having at least one aliphatic group having 8 to 16 carbon atoms.

6. The organic phosphate compound according to claim 3, wherein the connecting group is an organic group having 8 or more carbon atoms and at least one aromatic group.

7. The organic phosphate compound according to any one of claims 1 to 6, wherein the 10% by weight methanol solution has an electric conductivity at 25° C. of 0.4 mS/cm or less.

8. A dental polymerizable composition comprising:
(a) an organic phosphate compound having at least one radically polymerizable double bond, at least one phosphate residue having one or two hydroxyl groups, and at least one hydrocarbon group having 4 or more carbon atoms in a molecule, wherein a 10% by weight methanol solution of the organic phosphate compound has an electric conductivity at 25° C. of 0.5 mS/cm or less, and/or the organic phosphate compound has a light transmittance at 455 nm of 90% or more; and
(b) a polymerizable monomer capable of copolymerizing with the organic phosphate compound.

9. A process for preparing a (meth)acrylic acid monoester monophosphate ester, comprising:
reacting 1 to 5 moles of a diol having 4 to 30 carbon atoms with 1 mole of a (meth)acrylic acid at a reaction ratio of the (meth)acrylic acid of 60 to 90% by mol, to give a reaction mixture comprising a (meth)acrylic acid monoester of the diol and a (meth)acrylic acid diester of the diol, the molar ratio of the (meth)acrylic acid monoester of the diol to the (meth)acrylic acid diester of the diol being 2 to 8; and
reacting the resulting (meth)acrylic acid monoester of the diol with a phosphorus oxychloride, to give the (meth)acrylic acid monoester monophosphate ester.

10. A process for preparing a (meth)acrylic acid ester monophosphate ester, comprising:
reacting a monohydroxy (meth)acrylic acid ester comprising one hydroxyl group, at least one (meth)acryl group, and an organic acid residue having at least one hydrocarbon group having 4 to 30 carbon atoms, with a phosphorus oxychloride in the presence of an amine compound, to give a reaction mixture comprising the (meth)acrylic acid ester monophosphate ester, a chloride of (meth)acrylic acid ester monophosphate ester, and an amine salt;
washing the reaction mixture with an acidic aqueous solution to extract out the amine salt into an aqueous layer; and
washing the resulting reaction mixture with an aqueous solution of electrolytes made acidic by hydrogen chloride formed by hydrolysis of the chloride of (meth)acrylic acid ester monophosphate ester.

11. The process according to claim 10, wherein the step of giving the reaction mixture comprising the (meth)acrylic acid ester monophosphate ester, the chloride of (meth)acrylic acid ester monophosphate ester, and the amine salt comprises reacting the monohydroxy (meth)acrylic acid ester with a phosphorus oxychloride in the presence of the amine compound, to give the chloride of (meth)acrylic acid ester monophosphate ester; and thereafter reacting the chloride of (meth)acrylic acid ester monophosphate ester with water in the presence of the amine compound, to give a reaction mixture comprising the (meth)acrylic acid ester monophosphate ester and a trace amount of the chloride of (meth)acrylic acid ester monophosphate ester.

12. A process for preparing an organic phosphate compound, comprising subjecting a (meth)acrylate compound having at least one hydroxyl group as a raw material to phosphate esterification of hydroxyl group of the raw material with a phosphorus oxyhalide, wherein the (meth)acrylate compound is prepared by (meth)acrylic acid esterification of a polyol compound having an organic group having 4 or more carbon atoms and two or more hydroxyl groups in a molecule with a (meth)acrylic acid derivative while keeping at least one hydroxyl group, and wherein a content of a carbonyl compound in the polyol compound is 0.1% by mol or less.

13. The process according to claim 12, wherein the polyol compound is a diol having 4 to 30 carbon atoms.

14. A process for preparing a (meth)acrylic acid monoester monophosphate ester, comprising:
reacting 1 to 5 moles of a diol containing a carbonyl compound in an amount of 0.1% by mol or less, and having 4 to 30 carbon atoms with 1 mole of a (meth)acrylic acid, to give a reaction mixture comprising a (meth)acrylic acid monoester of the diol and a (meth)acrylic acid diester of the dial;
reacting the resulting (meth)acrylic acid monoester with a phosphorus oxychloride in the presence of an amine compound, to give a reaction mixture comprising the (meth)acrylic acid monoester monophosphate ester; and
washing the reaction mixture with an acidic aqueous solution and with an aqueous solution of electrolytes.

15. The process according to claim 14, wherein the step of giving the reaction mixture comprising the (meth)acrylic acid monoester monophosphate ester and the step of washing the reaction mixture with the acidic aqueous solution, and with the aqueous solution of electrolytes comprises:
reacting the (meth)acrylic acid monoester of the diol with a phosphorus oxychloride in the presence of the amine compound, to give a chloride of (meth)acrylic acid monoester monophosphate ester;
thereafter reacting the chloride of (meth)acrylic acid monoester monophosphate ester with water in the presence of the amine compound, to give a reaction mixture comprising the (meth)acrylic acid monoester monophosphate ester and a trace amount of the chloride of (meth)acrylic acid monoester monophosphate ester; and
subsequently washing the reaction mixture with an acidic aqueous solution to extract out an amine salt into an aqueous layer, and washing the resulting reaction mixture with an aqueous solution of electrolytes made acidic by hydrogen chloride formed by hydrolysis of the chloride of (meth)acrylic acid monoester monophosphate ester.

16. The process according to claim 14 or 15, wherein the reaction ratio of (meth)acrylic acid is from 60 to 90% by mol.

17. The process according to any one of claims 10, 11, 14 and 15, wherein the amine compound is used in an amount less than the stoichiometric amount, and thereby the reaction mixture contains the chloride of (meth)acrylic acid monoester monophosphate ester.

18. The process according to any one of claims 10, 11, 14 and 15, wherein washing with the aqueous solution is carried out under acidic conditions of pH of 3 or less.

19. The process according to any one of claims 13 to 15, wherein the content of the carbonyl compound in the diol is 0.05% by mol or less.

20. The process according to any one of claims 9 and 12 to 15, wherein a diol having an alkylene group of 8 to 16 carbon atoms is used.

21. The process according to any one of claims 9 and 13 to 15, wherein the diol is 1,10-decanediol.

22. The process according to claim 10 or 11, wherein the monohydroxy (meth)acrylic acid monoester is 10-methacryloyloxydecan-1-ol.

* * * * *